(12) United States Patent
Celentano et al.

(10) Patent No.: US 8,451,230 B2
(45) Date of Patent: May 28, 2013

(54) APPARATUS AND METHOD FOR REMOTELY CONTROLLING AN AMBULATORY MEDICAL DEVICE

(75) Inventors: Michael J. Celentano, Fishers, IN (US); Ulf Meiertoberens, Stocksund (SE); Peter Sabol, Fishers, IN (US); Raymond Strickland, Indianapolis, IN (US); Andreas Brand, Hasle b. Burgdorf (CH); Markus Oberli, Kirchberg (CH); Marcel Frikart, Bern (CH)

(73) Assignees: Roche Diagnostics International AG, Rotkreuz (CH); Roche Diagnostics Operations, Inc., Indianapolis, IN (US)

( * ) Notice: Subject to any disclaimer, the term of this patent is extended or adjusted under 35 U.S.C. 154(b) by 725 days.

(21) Appl. No.: 12/646,471

(22) Filed: Dec. 23, 2009

(65) Prior Publication Data
US 2010/0160860 A1    Jun. 24, 2010

Related U.S. Application Data

(63) Continuation of application No. PCT/US2008/066288, filed on Jun. 9, 2008.

(60) Provisional application No. 60/937,779, filed on Jun. 29, 2007, provisional application No. 60/937,933, filed on Jun. 29, 2007.

(51) Int. Cl.
*G06F 3/02* (2006.01)
*G06F 5/00* (2006.01)

(52) U.S. Cl.
USPC ............................................ 345/169; 604/67

(58) Field of Classification Search
USPC ............. 345/169, 660, 684; 604/66, 67, 504; 600/365; 607/60
See application file for complete search history.

(56) References Cited

U.S. PATENT DOCUMENTS

| 4,146,029 A | 3/1979 | Ellinwood, Jr. |
| 5,291,609 A | 3/1994 | Herz |

(Continued)

FOREIGN PATENT DOCUMENTS

| EP | 0079405 A1 | 5/1983 |
| EP | 0290683 A2 | 11/1988 |

(Continued)

OTHER PUBLICATIONS

The Bluetooth Forum: "Bluetooth security", Internet citation [online], Feb. 22, 2001. XP002171382. http://www.bluetooth.com/developer/specifiction/specification.asp.

(Continued)

*Primary Examiner* — Joe H Cheng
(74) *Attorney, Agent, or Firm* — Roche Diagnostics Operations, Inc.

(57) ABSTRACT

An electronic device may remotely control a medical device. The electronic device may include a wireless communication circuit configured to wirelessly communicate with the medical device, and a processor that receives from the medical device via the wireless communication circuit screen data generated by the medical device for display on a display device thereof and to control a display device of the electronic device according to the received screen data to display on the electronic device display the screen data generated by the medical device, to emulate at least some of a plurality of user keys of the medical device with selected ones of a plurality of user buttons of the electronic device, and to control the display device of the electronic device to display a map that relates emulated ones of the plurality of user keys to selected ones of the user buttons.

6 Claims, 11 Drawing Sheets

U.S. PATENT DOCUMENTS

| | | | |
|---|---|---|---|
| 5,364,346 | A | 11/1994 | Schrezenmeir |
| 5,748,103 | A | 5/1998 | Flach et al. |
| 5,943,633 | A * | 8/1999 | Wilson et al. ............... 702/45 |
| 5,997,475 | A | 12/1999 | Bortz |
| 6,289,421 | B1 | 9/2001 | Ali et al. |
| 6,554,798 | B1 * | 4/2003 | Mann et al. ............... 604/131 |
| 6,668,196 | B1 | 12/2003 | Villegas et al. |
| 6,852,104 | B2 * | 2/2005 | Blomquist ............... 604/504 |
| 6,909,439 | B1 | 6/2005 | Amro et al. |
| 6,985,870 | B2 * | 1/2006 | Martucci et al. ............... 705/3 |
| 7,399,277 | B2 * | 7/2008 | Saidara et al. ............... 600/300 |
| 7,645,258 | B2 * | 1/2010 | White et al. ............... 604/67 |
| 8,025,634 | B1 * | 9/2011 | Moubayed et al. ............... 604/65 |
| 8,127,046 | B2 * | 2/2012 | Grant et al. ............... 710/1 |
| 2001/0044731 | A1 | 11/2001 | Coffman et al. |
| 2003/0212379 | A1 * | 11/2003 | Bylund et al. ............... 604/504 |
| 2004/0078416 | A1 | 4/2004 | Kawasaki et al. |
| 2004/0167464 | A1 * | 8/2004 | Ireland et al. ............... 604/66 |
| 2004/0167465 | A1 * | 8/2004 | Mihai et al. ............... 604/67 |
| 2004/0248840 | A1 | 12/2004 | Hansen et al. |
| 2005/0065464 | A1 * | 3/2005 | Talbot et al. ............... 604/66 |
| 2005/0091577 | A1 | 4/2005 | Torres et al. |
| 2005/0162395 | A1 | 7/2005 | Unruh |
| 2006/0047192 | A1 * | 3/2006 | Hellwig et al. ............... 600/365 |
| 2006/0173406 | A1 | 8/2006 | Hayes et al. |
| 2006/0217061 | A1 | 9/2006 | Steele et al. |
| 2006/0224141 | A1 * | 10/2006 | Rush et al. ............... 604/503 |
| 2007/0109325 | A1 | 5/2007 | Eveleigh |
| 2007/0142767 | A1 | 6/2007 | Frikart et al. |

FOREIGN PATENT DOCUMENTS

| | | |
|---|---|---|
| EP | 1759726 A2 | 3/2007 |
| EP | 1788501 A1 | 5/2007 |
| EP | 1795116 A1 | 6/2007 |
| WO | 00/48112 A2 | 8/2000 |
| WO | 2004/099898 A2 | 11/2004 |
| WO | 2006/032653 A2 | 3/2006 |
| WO | 2006/046015 A1 | 5/2006 |
| WO | 2006/108304 A1 | 10/2006 |

OTHER PUBLICATIONS

Gehrmann, Christian, "Bluetooth Security White Paper, Bluetooth SIG", Bluetooth Doc, Apr. 19, 2002, pp. 1-46. XP003010085.

Levy, M., et al., "Fifo Memories Supply the Glue for High-Speed Systems", EDN Eleectrical Design News, Reed Business Information, Highlands Ranch, Co, US, vol. 42, No. 6, Mar. 14, 1997, pp. 65, 66, 68 and 70. XP 000695233.

Hastings, C., et al., "Future Trends in Fifo Architectures", Wescon Technical Papers, Western Periodicals Co., North Hollywood, CA, USA, vol. 36, Nov. 17, 1992, pp. 174-178. XP 000350089.

Rasid, M. F. A., et al., "Bluetooth Telemedicine Processor for Multichannel Biomedical Signal Transmission via Mobile Cellular Netowrks", IEEE Transactions on Information Technology in Biomedicine, IEEE Service Center, Los Alamitos, CA, USA, vol. 9, No. 1, Mar. 1, 2005, pp. 35-43. XP 011127538.

International Search Report and Written Opinion mailed Jul. 24, 2008 from PCT/US2008/066247.

International Search Report and Written Opinion mailed Oct. 30, 2008 from PCT/US2008/066288.

International Search Report and Written Opinion mailed Dec. 22, 2008 from PCT/US2008/066267.

International Search Report and Written Opinion mailed Jan. 9, 2009 from PCT/US2008/066248.

International Search Report and Written Opinion mailed Dec. 22, 2008 from PCT/US2008/066299.

International Search Report and Written Opinion mailed Jan. 14, 2009 from PCT/US2008/066331.

International Search Report and Written Opinion mailed Jan. 14, 2009 from PCT/US2008/066262.

* cited by examiner

| REMOTE DEVICE BUTTON FUNCTIONS IN REMOTE TERMINAL MODE ||
|---|---|
| REMOTE DEVICE BUTTON | PUMP KEY |
| 144 | 134 |
| 146 | 136 |
| 148 | MENU 130 |
| 150 | ✓ 132 |
| 154 | MENU 130 AND 134 |
| 152 | RETURN TO MAIN MENU |
| 148 144 AND | MENU 130 AND 134 |

FIG. 6

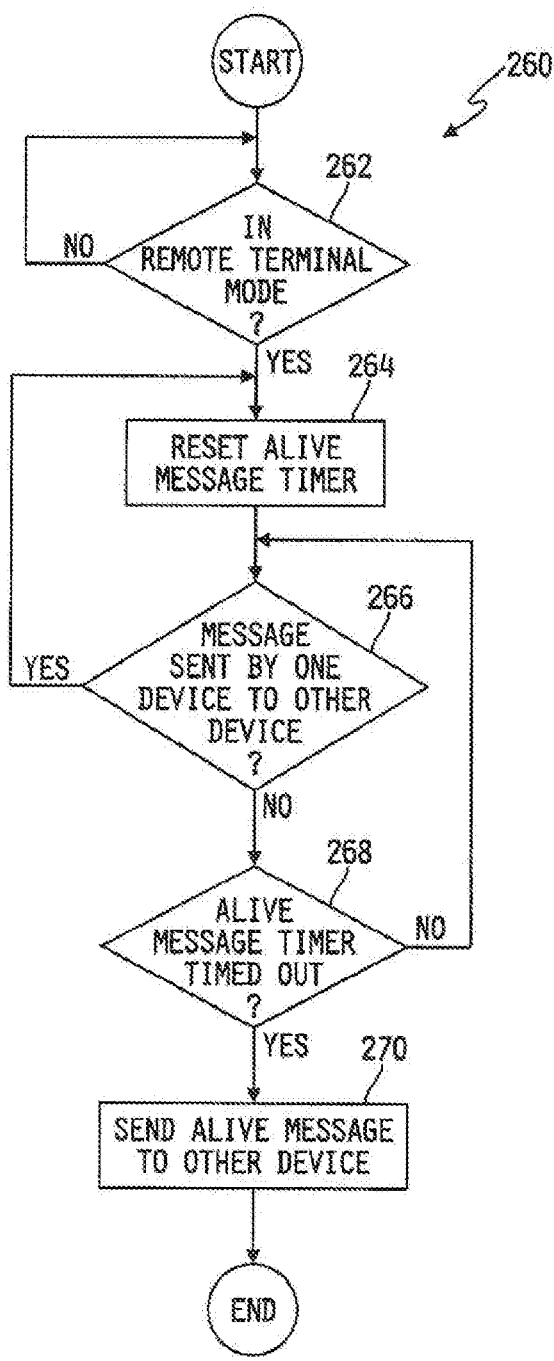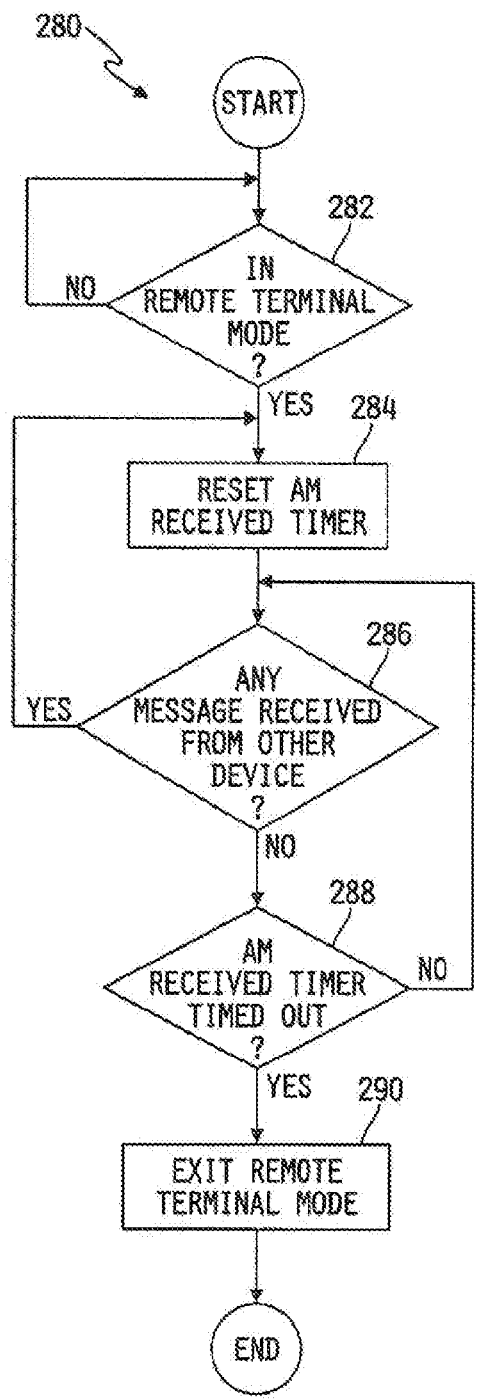
FIG. 9A
FIG. 9B

APPARATUS AND METHOD FOR REMOTELY CONTROLLING AN AMBULATORY MEDICAL DEVICE

REFERENCE

This application is a continuation of PCT/US2008/066288 filed Jun. 9, 2008 which is based on, and claims priority to U.S. Provisional Patent Application Ser. No. 60/937,779 and U.S. Provisional Patent Application Ser. No. 60/937,933, both filed Jun. 29, 2007, and all applications identified in this paragraph are hereby incorporated by reference.

FIELD

This disclosure relates generally to electronic devices for wirelessly communicating with one or more other electronic devices, and more specifically to hand held devices configured to communicate with medical devices.

BACKGROUND

Electronic devices for wirelessly communicating with at least one medical device are known. It is desirable to be able to remotely control the medical device with a remote electronic device so that one or more functions of the medical device can be remotely controlled in real time.

SUMMARY

The present invention may comprise one or more of the features recited in the attached claims, and/or one or more of the following features and combinations thereof. An electronic device for remotely controlling a medical device having a first display device and a plurality of user keys may comprise a plurality of user buttons, a second display device, a wireless communication circuit configured to wirelessly communicate with the medical device, and a processor including a memory having instructions stored therein that are executable by the processor to receive from the medical device via the wireless communication circuit screen data generated by the medical device for display on the first display device and to control the second display device according to the received screen data to display on the second display device the screen data generated by the medical device, to emulate at least some of the plurality of user keys with selected ones of the plurality of user buttons, to control the second display device to display a map that relates emulated ones of the at least some of the plurality of user keys to selected ones of the plurality of user buttons and to remotely control operation of the medical device via the wireless communication circuit based on user selection of at least one of the plurality of buttons.

The instructions stored in the memory may further include instructions that are executable by the processor to control the second display device to display navigation on the second display device by the selected ones of the plurality of user buttons and to display user selection of items on the second display.

The instructions stored in the memory may further include instructions that are executable by the processor to send user selection of a single one of the plurality of user buttons to the medical device via the wireless communication circuit, to receive updated screen data from the medical device via the wireless communication circuit if implementation of the sent user selection causes the medical device to modify the screen data generated by the medical device, and to control the second display device according to the updated screen data.

The instructions stored in the memory may further include instructions that are executable by the processor to receive updated screen data from the medical device via the wireless communication circuit if the operation of the medical device, apart from processing user selection of one of the plurality of user buttons, causes the medical device to modify the screen data generated by the medical device, and to control the second display device according to the updated screen data.

An electronic device for remotely controlling a medical device having a first display device and a plurality of user keys may comprise a plurality of user buttons, a second display device, a wireless communication circuit configured to wirelessly communicate with the medical device, and a processor including a memory having instructions stored therein that are executable by the processor to emulate at least some of the plurality of user keys with selected ones of the plurality of user buttons, to remotely control operation of the medical device via the wireless communication circuit based on user selection of at least one of the plurality of buttons, and to disregard user selections of any of the plurality of user buttons until acknowledgment is received from the medical device via the wireless communication circuit that the user selection of the single one of the plurality of user buttons was received and acted upon by the medical device.

The electronic device may further comprise an audible indicator, and a vibratory indicator. The instructions stored in the memory may further include instructions that are executable by the processor to activate at least one of the audible indicator and the vibratory indicator when the acknowledgment is received from the medical device that the user selection of the single one of the plurality of user buttons was received and acted upon by the medical device.

An electronic device for remotely controlling a medical device may comprise at least one of an audible indicator and a vibratory indicator, a wireless communication circuit configured to wirelessly communicate with the medical device, and a processor configured to remotely control the medical device in a remote terminal operating mode, the processor including a memory having instructions stored therein that are executable by the processor to receive a message from the medical device via the wireless communication circuit after power up of the electronic device and to automatically enter the remote terminal operating mode and activate the at least one of the audible indicator and the vibratory indicator based on the message if the message indicates a medical device alarm or error condition.

A medical device may comprise a display device, a plurality of user keys, a wireless communication circuit configured to transmit wireless signals and to receive wireless and remotely generated signals, and a processor including a memory having instructions stored therein that are executable by the processor to generate screen data for display on the display device, to transmit the screen data via the wireless communication circuit, to control the display device to display a predefined screen that is different from the screen data, and to implement remotely generated and wirelessly received medical device commands, in response to a remotely generated and wirelessly received command to be remotely controlled.

The instructions stored in the memory may further include instructions, that are executable by the processor to control the display device to display an image that is indicative of whether a wireless communication link is established with a remote electronic device.

The instructions stored in the memory may further include instructions that are executable by the processor to transmit along with the screen data either of alarm data that corresponds to one or more active alarm conditions of the medical device and error data that corresponds to one or more active error conditions of the medical device.

A medical system may comprise a medical device including a first display device, a first wireless communication circuit configured to transmit wireless signals and to receive wireless and remotely generated signals, and a first processor including a first memory having instructions stored therein that are executable by the processor generate screen data for display on the display device, to transmit the screen data via the wireless communication circuit, and to control the first display device to display a predefined screen that is different from the screen data, and a remote electronic device including a second display device, a second wireless communication circuit configured to transmit wireless signals and to receive wireless and remotely generated signals, and a second processor including a second memory having instructions stored therein that are executable by the processor to receive the screen data from the medical device via the second wireless communication circuit and to control the second display device to display the screen data generated by the first processor.

The medical device may further comprise a plurality of user keys and the remote electronic device may further comprise a plurality of user buttons. The second memory may further include instructions stored therein that are executable by the second processor to emulate at least some of the plurality of user keys with selected ones of the plurality of user buttons, and to control the second display device to display navigation on the second display device via the selected ones of the plurality of user buttons and to display user selection of items on the second display device via the selected ones of the plurality of user buttons.

A medical system may comprise a medical device configured to be remotely controlled in a remote terminal operating mode and a remote electronic device configured to remotely control the medical device in the remote terminal operating mode. The medical device may include a first wireless communication circuit configured to transmit wireless signals and to receive wireless and remotely generated signals, and a first processor including a first memory having instructions stored therein that are executable by the first processor reset an alive timer each time the first processor transmits a message via the first wireless communication circuit and to transmit an alive message via the first wireless communication circuit if the alive timer times out between transmission of messages via the first wireless communication circuit. The remote electronic device may include a second, wireless communication circuit configured to transmit wireless signals and to receive wireless and remotely generated signals, and a second processor including a second memory having instructions stored therein that are executable by the second processor reset an alive message timer each time the second processor receives via the second wireless communication circuit a message transmitted by the first processor via the first wireless communication circuit, and to exit the remote terminal operating mode if the alive message timer times out between receiving via the second wireless communication circuit messages transmitted by the first processor via the first wireless communication circuit.

A medical system may comprise a medical device configured to be remotely controlled in a remote terminal operating mode and a remote electronic device configured to remotely control the medical device in the remote control operating mode. The remote electronic device may include a first wireless communication circuit configured to transmit, wireless signals and to receive wireless and remotely generated signals, and a first processor including a first memory having instructions stored therein that are executable by the first processor reset an alive timer each time the first processor transmits a message via the first wireless communication circuit and to transmit an alive message via the first wireless communication circuit if the alive timer times out between transmission of messages via the first wireless communication circuit. The medical device may include a second wireless communication circuit configured to transmit wireless signals and to receive wireless and remotely generated signals, and a second processor including a second memory having instructions stored therein that are executable by the second processor reset an alive message timer each time the second processor receives via the second wireless communication circuit a message transmitted by the first processor via the first wireless communication circuit, and to exit the remote terminal operating mode if the alive message timer times out between receiving via the second wireless communication circuit messages transmitted by the first processor via the first wireless communication circuit.

A medical device may be configured to be remotely controlled in a remote terminal operating mode. The medical device may comprise a plurality of user keys, and a processor including memory having instructions stored therein that are executable by the processor to monitor one or more of the plurality of user keys while operating in the remote terminal operating mode and to exit the remote terminal operating mode upon detection of a user press of at least one of the one or more of the plurality of user keys if the plurality of user keys are unlocked.

The medical device may further comprise a display device. The instructions stored in the memory may further include instructions that are executable by the processor to control the display device to display a key combination that unlocks the plurality of user keys upon detection of the user press of at least one of the one or more of the plurality of user keys if the plurality of user keys are locked, and to exit the remote terminal operating mode upon detection of user press of the key combination.

A medical device may be configured to be remotely controlled in a remote terminal operating mode. The medical device may comprise a plurality of user keys, and a processor programmable in the remote terminal operating mode to implement delivery an immediate bolus of liquid to a body of a user. The processor may include a memory having instructions stored therein that are executable by the processor to monitor one or more of the plurality of user keys while implementing the delivery of the immediate bolus in the remote terminal operating mode, and to exit the remote terminal operating mode upon detection of a user press of at, least one of the one or more of the plurality of user keys.

The instructions stored in the memory may further include instructions that are executable by the processor to cancel the immediate bolus if upon detection of user press and hold of the at least one of the one or more of the plurality of user keys for a least a predefined time period.

In any of the embodiments, the medical device may be or, include a liquid infusion pump.

BRIEF DESCRIPTION OF THE DRAWINGS

FIG. 6 shows a table of one illustrative map for mapping user keys of the liquid infusion pump to buttons of the remote electronic device during a remote terminal operating mode of the liquid infusion pump via the remote electronic device.

FIGS. 9A and 9B show flowcharts of one illustrative embodiment of a pair of process for maintaining the liquid infusion pump and the remote electronic device wirelessly connected during the remote terminal operating mode.

DETAILED DESCRIPTION

For the purposes of promoting an understanding of the principles of the invention, reference will now be made to a number of illustrative embodiments shown in the attached drawings and specific language will be used to describe the same.

The following co-pending patent applications are incorporated herein by reference: PCT Patent Application No. PCT/US2008/066262, entitled COMBINATION COMMUNICATION DEVICE AND MEDICAL DEVICE FOR COMMUNICATING WIRELESSLY WITH A REMOTE MEDICAL DEVICE; PCT Patent Application No. PCT/US2008/066331, entitled METHOD AND APPARATUS FOR DETERMINING AND DELIVERING A DRUG BOLUS; PCT Patent Application No. PCT/US2008/066267, entitled LIQUID INFUSION PUMP; PCT Patent Application No. PCT/US2008/066299, entitled USER INTERFACE FEATURES FOR AN ELECTRONIC DEVICE; PCT Patent Application No. PCT/US2008/066247, entitled. METHOD FOR PAIRING AND AUTHENTICATING ONE OR MORE MEDICAL DEVICES AND ONE OR MORE REMOTE ELECTRONIC DEVICES; PCT Patent Application No. PCT/US2008/066248, entitled DEVICE AND METHODS FOR OPTIMIZING COMMUNICATIONS BETWEEN A MEDICAL DEVICE AND A REMOTE ELECTRONIC DEVICE; and U.S. Provisional Patent Application Ser. No. 61/130,855, entitled DEVICE AND METHODS FOR OPTIMIZING COMMUNICATIONS BETWEEN AN ELECTRONIC DEVICE AND A MEDICAL DEVICE.

Figure 1:
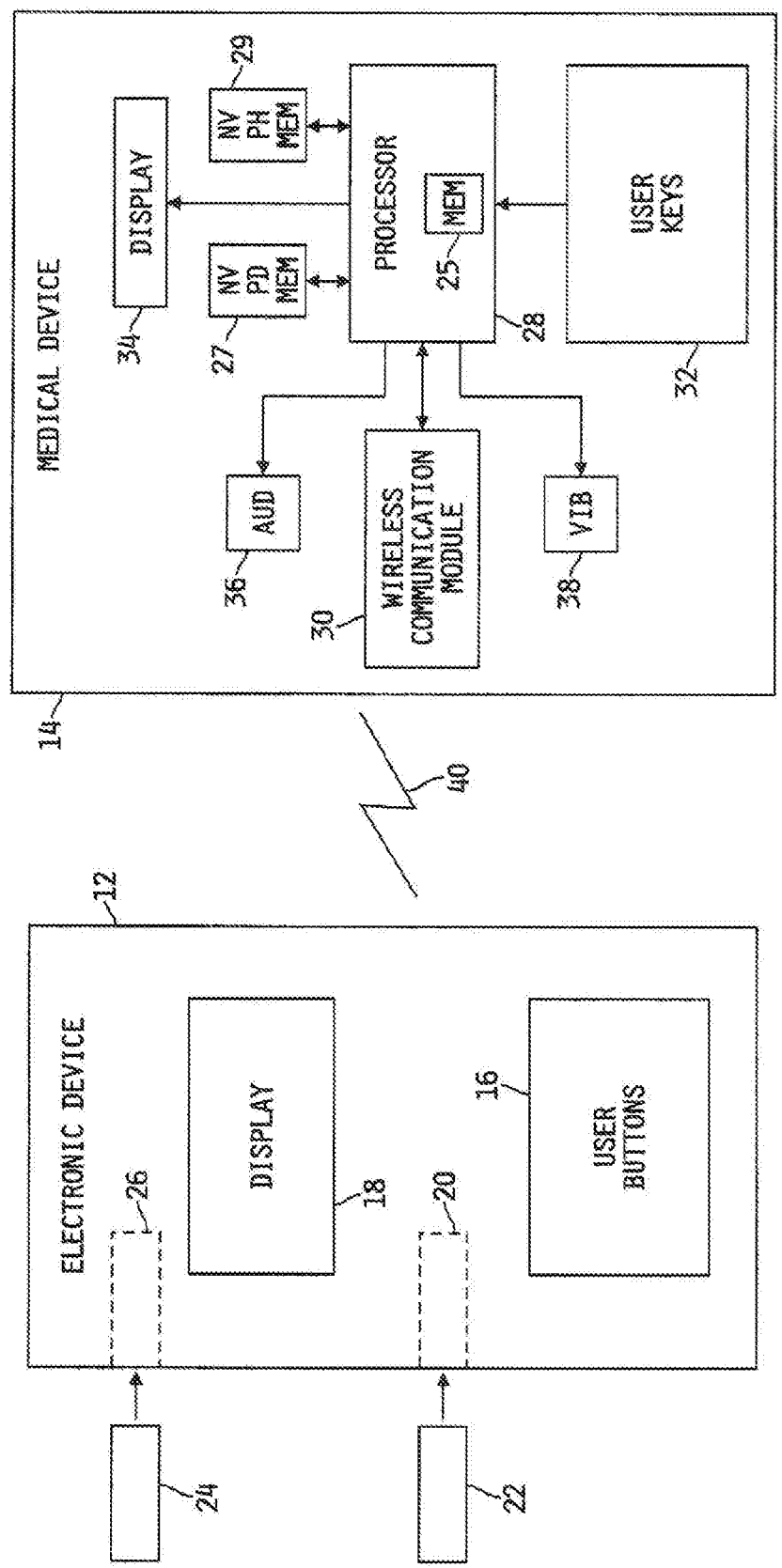
FIG. 1 shows a block diagram of one illustrative embodiment of a wireless communication system including a medical device and a remote electronic device that are both configured to wirelessly communicate with each other.

Referring now to FIG. 1, a block diagram is shown of one illustrative embodiment of a wireless communication system 10 including a remote electronic device 12 and medical device 14 that are both configured to wirelessly communicate with each other. The remote electronic device 12 has a housing through which a user button section 16 extends. In one embodiment, the user button section 16 defines a number of user buttons, keys or switches that may be manually manipulated by a user to provide input to the remote electronic device 12. A visual display unit 18 is carried by the housing of the electronic device 12, and in one embodiment the visual display unit 18 is provided in the form of a conventional liquid crystal display (LCD), although this disclosure contemplates using other conventional display units. Examples include, but are not limited to, plasma displays, light emitting diode (LED) based displays, vacuum fluorescent (VF) displays, and the like. In any case, the visual display unit 18 is controlled by the electronic device 12 to display information to a user of the device 12. In alternative embodiments, the user button section 16 may be or include one or more touch-sensitive buttons. In this embodiment, one or more touch-sensitive buttons may, but not, form part of the display unit 18.

The electronic device 12 further includes a carrier port 20 that extends into the housing from an opening defined therein. The carrier port 20 is sized to receive therein a sample carrier or strip 22 upon which a liquid sample containing, an analyte has been or will be deposited. The electronic device 12 includes electrical circuitry that analyzes the liquid sample deposited on the sample carrier 22, when the sample carrier 22 is received within the carrier port 20, to determine a concentration of the analyte contained in the liquid sample. In one embodiment; the liquid sample is blood and the analyte is glucose. In this embodiment, the sample carrier 22 may is illustratively provided in the form of a glucose test strip, and the electrical circuitry of the electronic device 12 includes conventional circuitry that measures the concentration of glucose in a blood sample deposited on the test strip 22. In alternative embodiments, the liquid sample may be or include other bodily fluids, and the analyte may be any analyte that is contained in a bodily fluid.

In the embodiment illustrated in FIG. 1, the electronic device 12 further includes a conventional data, key port 26 that extends into the housing from an opening defined therein. The data key port 26 defines an electrical interface or connector therein that is configured to electrically connect to a complementarily configured electrical interface or connector defined on a conventional data key 24. The data key 24 includes a conventional memory device (not shown) that is electrically connected to the electrical interface or connector defined on the data key 24. The memory device, e.g., ROM key, is electrically connected to the electrical circuitry of the electronic device 12 via the electrical interface defined on the data key 24 and the electrical interface defined in the data key port 26 when the data key 26 is received within the data key port 24. Generally, the memory device of the data key 24 has calibration data stored therein that is specific to a lot or batch of test strips 22, and the electrical circuitry of the electronic device 12 uses the calibration data stored in the memory device of the data key 24 to correct glucose concentration measurements when using a test strip 22 from a corresponding lot or batch of test strips as is known in the art. Typically, each lot or batch of test strips 22 purchased by a user will include a dedicated data key 24 that is to be used when measuring glucose concentration with that lot or batch of strips.

It will be understood that while the carrier port 20, sample carrier 22 and electrical circuitry of the electronic device 12 have been described in one embodiment as being configured to measure the glucose concentration of blood samples deposited on the sample carrier 22, this disclosure contemplates other embodiments in which the carrier port 20, sample carrier 22 and/or electrical circuitry of the electronic device 12 is/are configured to measure other analytes in other liquid samples.

The medical device 14 includes a conventional processor 28 that is electrically connected to a wireless communication circuit 30. The processor 28 includes a conventional memory unit 25 which has stored therein a number of processes in the form of instructions that are executable by the processor 28 to control operation of the medical device 14 and to wirelessly communicate with the electronic device 12. In the illustrated embodiment, the medical device 14 further includes conventional non-volatile memory units 27 and 29. In one embodiment, the non-volatile memory unit 27 is provided in the form of a conventional ferroelectric random access memory (FRAM) and the non-volatile memory unit 29 is provided in the form of a conventional electrically erasable programmable read only memory (EEPROM), although either memory unit 27, 29 may alternatively be provided in the form of one or more other conventional non-volatile memory units. In any case, the memory units 27 and 29 are each external to the processor 28 and are each electrically connected to the processor 28. In one illustrative embodiment in which the medical device is a drug infusion pump, as will be described in greater detail hereinafter, the memory unit 27 is a pump delivery (PD) memory unit in which the processor 28 stores current pump delivery information, and the memory unit 29 is a pump history (PH) memory unit that has stored therein pump history information, e.g., in the form of event records each corresponding to an operational event of the pump 14. The medical device 14 further includes a wireless communication circuit 30 that is configured to communicate wirelessly with a similar wireless communication module of the remote electronic device 12 via a wireless communication link 40 in a conventional manner. In one embodiment, as will be illustrated by example throughout this disclosure, the wireless communication circuit 30 and the wireless communication module of the electronic device 12 are both conventional BlueTooth® modules configured to wirelessly communicate according to a conventional BlueTooth® communication protocol. It will be understood, however, that the wireless communication circuit or module 30 and the wireless communication module of the electronic device 12 may alternatively be configured to wirelessly communicate according to one or more other communication protocols.

The medical device 14 illustratively includes a housing through which a number of user keys 32 extend. The user keys 32 may be provided in the form of any number of user selectable buttons, keys or switches that are electrically connected to the processor 28. The medical device 14 further includes a visual display unit 34 that is carried by the housing and that is electrically connected to the processor 28. The visual display unit 34 may be, for example, a conventional liquid crystal display (LCD), plasma displays, light emitting diode (LED) based display, vacuum fluorescent (VF) display, or the like. The visual display unit 34 is controlled by the processor 28 to display information to a user of the medical device 14. In alternative embodiments, the user keys 32 may be or include one or more touch-sensitive buttons. In this embodiment, one or more touch-sensitive buttons may, but not, form part of the display unit 34.

The processor 28 of the medical device 14 is further electrically connected to a conventional audible indication device 36 and to a conventional vibratory device 38. The processor 28 is generally operable to control the audible indication device 36 and the vibratory device 38 to produce one or more audible sounds and/or vibrations respectively to notify the user of various operational aspects of the medical device 14 and to also notify the user of any alarm and/or warning conditions associated with the medical device 14. In alternative embodiments, the medical device 14 may not include a display device 34 and/or user keys 32. In some such embodiments, the medical device 14 may include one or more visual indicators for conveying information to a user. Examples of such visual indicators may include, but should not be limited to, one or more lamps, one or more light, emitting diodes (LEDs), or the like.

In one illustrative embodiment, the medical device 14 is an ambulatory medical device. Examples of ambulatory medical devices include, but are not limited to, an implantable liquid delivery pump or a non-implantable liquid delivery pump, such as a drug infusion pump, an implantable or non-implantable body condition sensor or sensor system, or the like. In embodiments in which the electronic device 14 is a medication delivery pump, the medication delivered by such a pump may be or include, but should not be limited to, insulin or other conventional blood glucose modifying drug. In alternate embodiments, the liquid delivered by any such a pump may be or include, but should not be limited to, one or a combination of drugs, saline, one or a combination of perfusion fluids, or the like. Throughout this disclosure; the medical device 14 and operations associated with the medical device 14 will be described in the context of an insulin infusion pump, although it will be understood that the medical device 14 may alternatively be or include other medical devices and the following description therefore should not be considered to be limited to an liquid delivery pump generally, or to an insulin infusion pump specifically.

Figure 2:
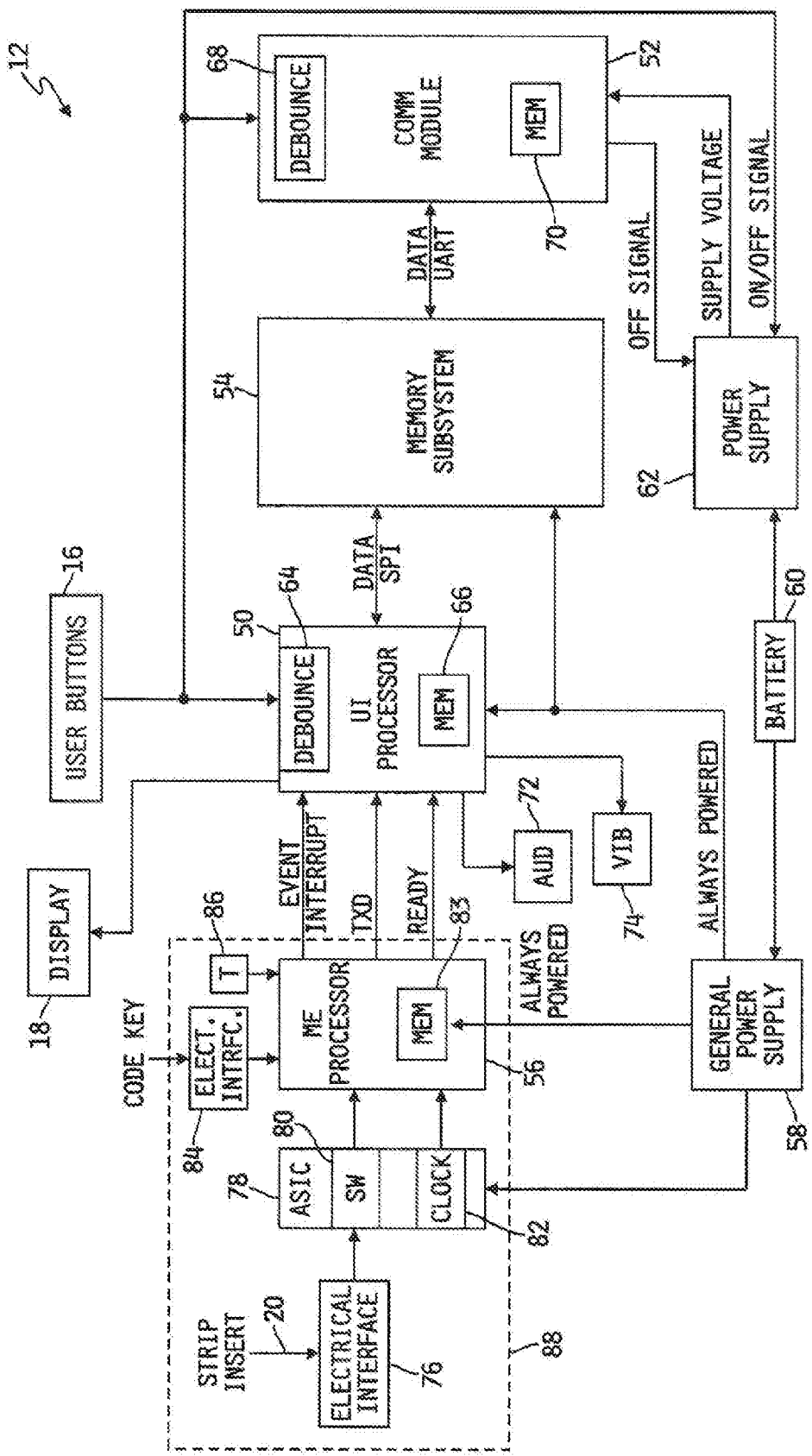
FIG. 2 shows a block diagram schematic of one illustrative embodiment of an electronic circuit that is carried by, and that controls, the remote electronic device of FIG. 1.

Referring now to FIG. 2, a block diagram schematic is shown of one illustrative embodiment of an electronic circuit that is carried by, and that controls, the remote electronic device 12 of FIG. 1. In the illustrated embodiment, the electronic circuit includes four modules with separate and distinct functional responsibilities. For example, the electronic circuit includes a User Interface (UI) processor 50 that is the main controller of the electronic device 12. In addition to processing all aspects of the user interfaces, such as user button section 16, or display unit 18, it is the origination and destination of all data communicated from and to the insulin infusion pump 14. As will be described in greater detail herein, the UI processor 50 has no control over operation of the wireless communication circuit of the remote electronic device 12. The UI processor 50 operates according to a UI clock signal that is generated internally to the UI processor 50. The UI processor 50 includes a memory unit 66 having instructions stored therein that are executable by the UI processor 50 to control operations associated with the remote electronic device 12. In one illustrative embodiment, the UI processor 50 is a UPD70F3719GC 32-bit microcontroller that is commercially available from NEC Electronics America of Santa Clara, Calif., although this disclosure contemplates other implementations of the UI processor 50.

The electronic circuit of FIG. 2 further includes a wireless communication circuit 52 that is exclusively responsible for the control of all wireless communications with one or more external electronic devices but that does not control any other operations associated with the electronic device 12. The wireless communication circuit 52 operates from a clock signal that is generated internally to the wireless communication circuit 52 and that is not synchronized to the UI clock signal from which the UI processor 50 operates. Operation of the wireless communication circuit 52 is therefore asynchronous with respect to the operation of the UI processor 60. In one illustrative embodiment, the wireless communication circuit 52 is provided in the form of a conventional BlueTooth® telemetry module that includes a conventional processor and a memory unit 70, and that further includes conventional wireless communication hardware such as a suitable antenna. The memory unit 70 illustratively has stored therein instructions that are executable by the processor of the wireless communication circuit 52 to exclusively control of all wireless communications with external devices, such as the insulin infusion pump 14. In one illustrative embodiment, the wireless communication circuit 52 is a BC419143B BlueCore™ 4-Flash Plug-n-Go™ single chip BlueTooth® radio and baseband integrated circuit for BlueTooth® 2.4 GHz systems that is commercially available from CSR of Richardson, Tex., although this disclosure contemplates other implementations of the wireless communication circuit 52. Alternatively, as described hereinabove, this disclosure contemplates embodiments in which the wireless communication module 52 is configured for wirelessly communication according to wireless communication protocols other than BlueTooth®.

As illustrated in FIG. 2, the UI processor 50 and the wireless communication module 52 each include debounce circuitry 64 and 68 respectively that is electrically connected to the user buttons 16. The debounce circuitry 64, 68 is conventional in that it reduces the sensitivity of the processors 50 and wireless communication circuit 52 to spurious switching events associated with the user buttons 16, thereby increasing the likelihood that only actual button presses are detected by the processors 50 and 52.

The electronic circuit illustrated in FIG. 2 further includes a memory subsystem 54 that is electrically connected to the UI processor 50 and also to the wireless communication circuit 52. The memory subsystem 54 is generally operable to store, at least temporarily, data moving between the UI processor 50 and the wireless communication circuit 52. Data communication between the memory subsystem 54 and the UI processor 50 is illustratively carried out via a serial peripheral interface, SPI, in which case the transfer of data between the memory subsystem 54 and the UI processor 50 is synchronous with a data transfer clock, SCLK, of the UI processor 50. Illustratively, data communication between the memory subsystem 54 and the wireless communication circuit 52 is carried out via a universal asynchronous receiver/transmitter (UART) interface, in which case the transfer of data between the memory subsystem 54 and the wireless communication circuit 52 is asynchronous. In some alternative embodiments, the data transfer interfaces may be interchanged such that data transfer between the memory subsystem 54 and the UI processor 50 is asynchronous and data transfer between the memory subsystem 54 and the wireless communication circuit 52 is synchronous.

The memory subsystem 54 temporarily stores data moving between the UI processor 50 and the wireless communication circuit 52. In some embodiments, the memory subsystem 54 does not control other circuitry, and in some such embodiments the memory subsystem 54 may be provided in the form of a conventional memory device. In other embodiments in which the memory subsystem 54 does or does not control other circuitry, the memory subsystem 54 may be provided in the form of a conventional processor that is configured to operate as a Dual-Port RAM (DPR) processor. In such embodiments, the DPR processor 54 operates from a clock signal that is separate from the UI clock signal from which the UI processor 60 operates. In one illustrative embodiment, such a DPR processor 54 is a MC9S08GT16A 8-bit microcontroller unit that is commercially available from Freescale Semiconductor, Inc, of Austin, Tex., although this disclosure contemplates other implementations of the memory subsystem 54 that is provided in the form of a conventional processor configured as a DPR processor 54.

The electronic circuit illustrated in FIG. 2 further includes a Measurement Engine (ME) processor 56 that controls analyte concentration measurements of liquid samples contained on test elements 22, e.g., blood glucose measurements, and that reports the analyte concentration measurement results to the UI processor 50. The ME processor 56 includes a memory unit 83 having instructions stored therein that are executable by the ME processor 56 to control analyte measurement operations. The ME processor 56 operates from an internally generated clock signal that is separate from the clock signal from which the UI processor 50 operates. The ME processor 56 is electrically connected to the UI processor 50 via an Event Interrupt line, TXD (data transmission) line and a Ready line. The Event Interrupt line is illustratively used by the ME processor 56 to notify the UI processor of analyte measurement events, such as a strip insert event in which a user initiates an analyte measurement. The TXD line is used by the ME processor 56 to transmit analyte measurement data to the UI processor 50 for display on the display unit 18, for storage thereof in a history database and/or for use in conducting other operations. The Ready line is used by the ME processor 56 to notify the UI processor 50 of the operational state, e.g., measuring or not measuring analyte concentration, of the ME processor. In one illustrative embodiment, the ME processor 56 is a MSP430T2AIPEG mixed-signal microcontroller unit that is commercially available from Texas Instruments, Inc. of Dallas, Tex., although this disclosure contemplates other implementations of the ME processor 56.

As illustrated in FIG. 2, the ME processor 56, along with other electrical components, form an analyte measuring facility 88, e.g., a glucose meter. In addition to the ME processor 56, the analyte measuring facility 88 further includes an application specific integrated circuit (ASIC) 78 that is electrically connected to the ME processor 56 and also to an electrical interface 76 within the carrier port 20. In one illustrative embodiment, when a sample carrier 22, e.g., a glucose test strip, is inserted into the carrier port 20, electrical contacts on the sample carrier 22 contact the electrical interface 76 to thereby electrically connect the sample carrier 22 to the ASIC 78. A switch 80 contained in the ASIC is triggered by insertion of the carrier 22 into the carrier port 20, and an output of the switch 80 thus notifies the ME processor 56 of insertion of a carrier 22 into the carrier port 20. The ASIC 78 further illustratively includes a clock circuit 82 that is programmable for a number of different functions. For example, the clock circuit 82 may be programmed to generate a signal to automatically turn on, e.g., power up, the device 12 at one or more programmable times. As another example, the clock circuit 82 may be programmed to generate a signal corresponding to one or more reminders. Other examples will occur to those skilled in the art, and such other examples are contemplated by this disclosure. In any case, the signal generated by the clock circuit 82 is provided to the ME processor 56, and the ME processor 56 is responsive to the receipt of this signal to power up from a sleep state if the ME processor 56 is in such a sleep state, and to produce an event interrupt signal on the Event Interrupt line. The event interrupt signal is received by the UI processor 50, which then powers up from a sleep state if the UI processor 50 is in such a sleep state, and/or generates an audible or visible reminder corresponding to any reminder time programmed in the clock circuit 82.

As illustrated in FIG. 2, the analyte measuring facility 88 further includes another electrical interface 84 that is positioned within the code key port 26. Illustratively, when a code key 24 is received within the code key port 26, electrical contacts on the code key 24 electrically connect with the electrical interface 84 so that the ME processor 56 may read the calibration information stored in the memory device of the code key 24. The analyte measuring facility 88 further includes a temperature sensor 86 that is electrically connected to the ME processor 56. In one, illustrative embodiment, the temperature sensor 86 is provided in the form of a conventional thermistor, although this disclosure contemplates other embodiments in which the temperature sensor 88 may be or include one or more other conventional temperature sensors. In any case, the ME processor 56 is operable to receive a temperature signal from the temperature sensor 86 that corresponds to an operating temperature of the analyte measuring facility. In one illustrative embodiment, the memory 83 has instructions stored therein that are executable by the ME processor 56 to disable, i.e., not conduct, analysis of an analyte containing sample if the temperature signal produced by the temperature sensor 86 indicates that the temperature of the analyte measuring facility 88 is less than a threshold temperature. In such cases, the ME processor 56 is further operable, pursuant to the instructions stored in the memory 83, to inform the UI processor 50 that the analyte measuring facility is so disabled, and the UI processor 50 is operable, pursuant to instructions stored in the memory unit 66, to control the display device 18 to display a message indicating that the temperature is too low to conduct analyte concentration measurements.

The electronic circuit illustrated in FIG. 2 further includes a general power supply 58 that provides a supply voltage to the ASIC 78, the ME processor 56, the UI processor 50 and the memory subsystem 54 on a continuous basis. The supply voltage is derived by the general power supply circuit 58 from one or a series or parallel combination of rechargeable or non-rechargeable batteries (BATTERY) 60.

A dedicated power supply 62 provides a supply voltage, which is also derived from the one or series or parallel combination of rechargeable or non-rechargeable batteries (BATTERY) 60, to the wireless communication module 52. The power supply 62 receives one control input from the user buttons 16, and in the illustrated embodiment the power supply 62 may be powered on and off via one or a combination of the user buttons 16 via the one control input. The power supply 62 also receives another control input from the wireless communication circuit 52, and in the illustrated embodiment the power supply 62 may be turned off by the wireless communication circuit 52 via the other control input.

In addition to the display 18, the UI processor 50 is electrically connected to a conventional audible indication device 72 and also to a conventional vibratory device 74. The UI processor 50 is generally operable to control the audible indication device 72 and the vibratory device 74 to produce one or more audible sounds and/or vibrations respectively to provide for the capability of the device 12 to produce corresponding audible and/or tactile notifications, i.e., alarms or the like. In one embodiment, the audible indication device 72 is a tone generator that produces a beep or other tone when activated, although the audible indication device 72 may alternatively or additionally be or include one or more other conventional audible indication devices.

Figure 3:
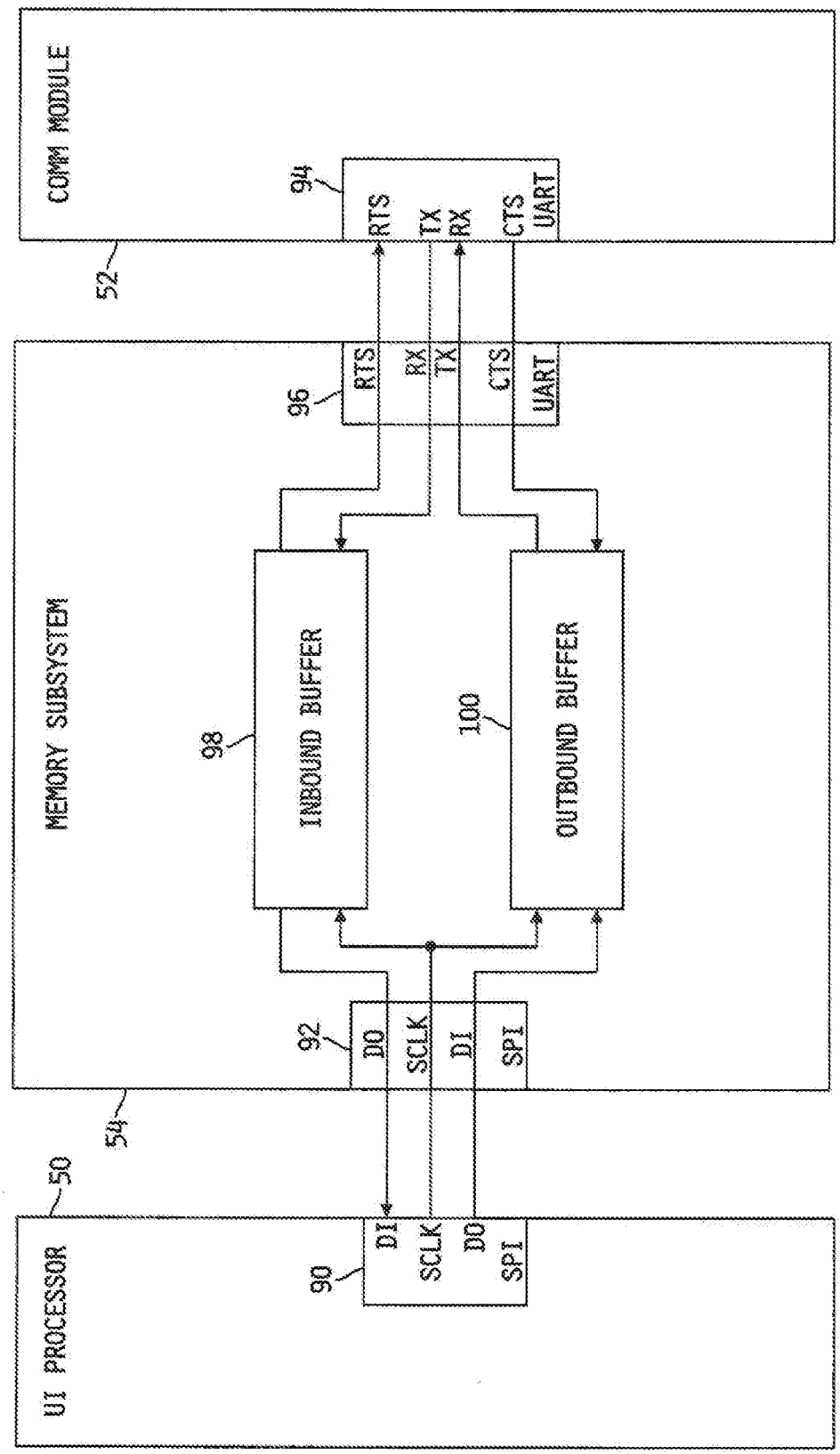
FIG. 3 shows a block diagram schematic of some of the details of one illustrative embodiment of the memory subsystem of the remote electronic device of FIG. 2.

Generally, the memory subsystem 54 acts as an independent repository of data packets moving between the UI processor 50 and the wireless communication circuit 52. Referring to FIG. 3, a block diagram of some of the details of the memory subsystem 54 is shown along with electrical connections to the UI processor 50 and to the wireless communication circuit 52. In the illustrated embodiment, the memory subsystem 54 is provided in the form of a DPR processor as described above, and FIG. 3 will be described in this context, although it will be understood that the memory subsystem 54 may alternatively be provided in other forms as described above.

In the embodiment illustrated in FIG. 3, one of the dual ports of the DPR processor 54 is a serial peripheral interface (SPI) port 92 that is electrically connected to a serial peripheral interface port 90 of the UI processor 50 via a conventional serial communications interface. The serial communications interface operates from a serial clock signal, SCLK, (e.g., 125 kHz) that is derived from the UI clock signal. Transfer of inbound and outbound data between the SPI port 90 of the UI processor 50 and the SPI port 92 of the DPR processor 54 is controlled by the UI processor 50 using the serial clock signal, SCLK, so that data transfer between the two processors 50, 54 is synchronized.

The other of the dual ports of the DPR processor 54 is a universal asynchronous receiver/transmitter (UART) port 96 that is electrically connected to a UART port 94 of the wireless communication circuit 52 via a conventional asynchronous interface. Transfer of inbound and outbound data packets between the UART port 94 of the wireless communication circuit 52 and the UART port 96 of the DPR processor 54 (e.g., at 150 kbps) is controlled by the wireless communication circuit 52, and takes place asynchronously with respect to the transfer of inbound and outbound data between the SPI port of the UI processor 50 and the DRP processor 54.

The DPR processor 54 has an inbound data buffer 98 and an outbound data buffer 100 that are each accessible by the SPI and UART port 92 and 96 respectively of the DPR processor 54. The UART port 96 of the DPR processor 54 includes conventional clear to send (CTS) and ready to send (RTS) lines. The CTS line is monitored by the DPR processor 54 and the RTS line is monitored by the wireless communication circuit 52. The DPR processor 54 deactivates the UART RTS line whenever the inbound data buffer 98 is full, and otherwise activates the UART RTS line. The wireless communication circuit 52 activates the UART CTS line whenever the UART port of the wireless communication circuit 52 is requesting data, and otherwise deactivates the UART CTS line.

When data is to be sent by the UI processor 50 to an external device or system, e.g., the insulin infusion pump 14, the UI processor 50 first requests the state of the outbound data buffer 100 of the DPR processor 54. If the DPR processor 54 answers that its outbound data buffer 100 is "not full," the UI processor 50 transfers the data, or as much of the data as possible, to the outbound data buffer 100 of the DPR processor 54 via the data out (DO) line of the SPI port 90 at a rate determined by SCLK. If the DPR processor 54 instead answers that the outbound data buffer 100 is "full," the UI processor 50 waits for a time interval and then repeats the process of requesting the state of the outbound data buffer 100, etc.

Periodically with respect to the clock signal of the wireless communication circuit 52 and asynchronously with respect to the SCLK signal, the wireless communication circuit 52 requests data from the DPR processor 54 by activating the UART CTS line of the DPR processor 54. As long as the outbound data buffer 100 of the DPR processor 54 is empty, the wireless communication circuit 52 continues to periodically activate the UART CTS line. If the UART CTS line is active and the outbound data buffer 100 of the DPR processor 54 is not empty, the wireless communication circuit 52 retrieves the data from the outbound data buffer 100 of the DPR processor 54 via the RX line of the UART port 96. The DPR processor 54 illustratively transfers the data stored in its outbound data buffer 100 to its UART port 96 in a first received to last received order until the outbound data buffer 100 has been emptied or until the wireless communication circuit 52 deactivates the UART CTS line. The wireless communication circuit 52 then incorporates the data retrieved from the outbound data buffer 100 of the DPR processor 52, via the data UART, into to the wireless communication protocol structure, and wirelessly transmits the incorporated data via conventional wireless signal transmission circuitry contained within the wireless communication module 52. The wireless communication circuit 52 does not process, interpret or alter the contents of the data retrieved from the outbound data buffer 100 of the DPR processor 54, nor does it make any decisions or execute any steps based on the contents of the data. Rather, the wireless communication circuit 52 treats all such data the same, regardless of its contents, by incorporating the data into a predefined wireless communication protocol structure, e.g., BlueTooth® protocol structure, and then wirelessly transmitting the incorporated data using the predefined wireless communication protocol. Information transferred by the UI processor 50 to the memory subsystem 54, and then from the memory subsystem 54 to the wireless communication circuit 52 for wireless transmission to another electronic device is thus referred to as outbound information or data.

Inbound wireless signal transmissions from external, devices or systems, e.g., the insulin infusion pump 14, are received by the wireless communication circuit 52 via conventional wireless signal receiving circuitry of the wireless communication circuit 52. The wireless communication circuit 52 first isolates the inbound data from the wireless communication protocol structure, and then checks the status of the UART RTS line of the DPR processor 54. If the RTS line is activated, indicating that the inbound data buffer 98 of the DPR processor 54 is not full, the wireless communication circuit 52 sends the isolated data, or as much if the data as possible, to the UART port 96 of the DPR processor 54. The DPR processor 54 then places the data received at the UART port 96 into the inbound data buffer 98 of the DPR processor 54. If the UART RTS line is deactivated, indicating that the inbound data buffer 98 of the DPR processor 54 is full, the wireless communication circuit 52 waits for a time interval before rechecking the state of the UART RTS line.

Periodically, and asynchronously with respect to the operation of the wireless communication circuit 52, the UI processor 50 requests the state of the inbound data buffer 98 of the DPR processor 54 via the data in (DI) line of the SPI port 90. As long as the DPR processor 54 answers that the inbound data buffer 98 is empty, the UI processor 50 continues to periodically request the state of the inbound data buffer 98. If the DPR processor 54 answers that the inbound data buffer 98 of the DPR processor 54 contains data, the UI processor 50 retrieves the data from the inbound data buffer 98 of the DPR processor 52 via the data in (DI) line of the SPI port 90 using the SCLK signal, and then processes the data according to its contents. "Checking" the inbound and/or outbound data buffer 98, 100 of the DPR processor 54 by the wireless communication circuit 52 and/or UI processor 50, as this term may be used hereinafter, will generally refer to the process just described in the preceding several paragraphs. While FIGS. 2 and 3 illustrate an embodiment in which the interface between the UI processor 50 and the memory subsystem 54 is a synchronous interface and the interface between the wireless communication circuit 52 and the memory subsystem 54 is an asynchronous interface, this disclosure contemplates alternative embodiments in which the interface between the UI processor 50 and the memory subsystem 54 is an asynchronous interface and the interface between the wireless communication circuit 52 and the memory subsystem 54 is an synchronous interface or in which both interfaces are asynchronous or synchronous interfaces. In any case, it should be apparent that the UI processor 50 at all times operates independently and asynchronously with respect to the operation of the wireless communication circuit 52, and the wireless communication circuit 52 operates independently and asynchronously with respect to the operation of the UI processor 50 and also with respect to the operation of the DPR processor 54.

The UI processor 50 controls the display 18 of the electronic device 12 to indicate the connection status of the wireless communication module 52 relative to the wireless telemetry system of the insulin infusion pump 14. Upon power up of the electronic device 12, following activation of the power supply 62 via the user buttons 16 after being deactivated and under certain other operating conditions that will be described in greater detail hereinafter, the UI processor 50 attempts to establish a wireless connection with the insulin infusion pump 14. While a wireless connection is not established between the electronic device 12 and the insulin infusion pump 14, the UI processor 50 controls the display 18 to display a flashing (or fixed) icon to indicate that no wireless connection exists between the electronic device 12 and the insulin infusion pump 14. The UI processor 50 independently controls the display 18 in this manner without any information provided by the wireless communication module 52. The UI processor 50 then initiates establishment of a wireless connection between the remote electronic device 12 and the insulin infusion pump 14 by placing a message into the data buffer 100 of the outbound port of the memory subsystem 54, as described above. In this case, the message includes a wireless connection request, e.g., in the form of a command to transmit an acknowledgement response back to the electronic device 12. The wireless communication circuit 52 then transmits this message as described above. If the insulin infusion pump 14 is within range, the insulin infusion pump 14 receives the message and responds to the wireless connection request by wirelessly transmitting a message that includes an acknowledgement response. If the transmitted message is received by the electronic device 12, the wireless communication circuit 52 is operable as described above to isolate the message from the wireless communication protocol structure and to place the message in the data buffer 98 of the inbound port of the memory subsystem 54. The UI processor 50 then retrieves the message from the inbound port of the memory subsystem 54, processes the message to determine whether it contains an acknowledgement response. If the message contains an acknowledgement response, the UI processor 50 interprets this as indicating that a wireless connection is now established between the electronic device 12 and, the insulin infusion pump 14, and controls the display device 18 to display a fixed (or flashing) icon to indicate that a wireless connection is established between the electronic device 12 and the insulin infusion pump 14. The electronic device 12 periodically transmits a wireless connection status message to the infusion pump 14 in the above fashion at regular intervals. As long as the insulin infusion pump 14 responds as just described, the UI processor 50 controls the display 18 to display the fixed (or flashing) icon to indicate that a wireless connection exists between the electronic device 12 and the insulin infusion pump 14. If the UI processor 50 does not receive such a response within a predefined time period following storage of the acknowledgement response in the memory subsystem 52, the UI processor 50 controls the display 18 to display a flashing (or fixed) icon indicating that the wireless connection between the electronic device 12 and the insulin infusion pump 14 does not exist or no longer exists.

In the illustrated embodiment the power supply 62 is generally powered on as long as the wireless communication circuit 52 is communicating with either or both of the UI processor 50 or the insulin infusion pump 14, unless otherwise powered off manually by a user via the user buttons 16 or automatically by the wireless communication circuit 52. For example, the power supply 62 may be completely powered down, i.e., turned off, from any state via a simultaneous or sequential user press of a number of the user buttons 16. The power supply 62 remains in the completely powered down state until the user again presses the simultaneous or sequential number of the user buttons 16 or a different simultaneous or sequential user press of a number of the user buttons, or if the user powers down the electronic device 12 and then powers back up the electronic device 12.

While the power supply 62 is on and supplying the supply voltage to the wireless communication circuit 52, the wireless communication circuit 52 is responsive to a number of different events to transition itself into, and out of, any of a plurality of different low power states, and to also turn off the power supply 62 after being in a lowest power sleep state for a predefined time period of inactivity. For example, when in a fully powered "awake" state, the wireless communication circuit 52 is operable to periodically; e.g., every 100-200 milliseconds, check the outbound data buffer 100 of the memory subsystem 54 as described above. As another example, each time the wireless communication circuit 52 finds data to be sent in the outbound data buffer 100 of the memory subsystem 54, the wireless communication circuit 52 incorporates the data into the predetermined wireless communication protocol structure, and wirelessly transmits corresponding signals to the insulin infusion pump 14 as described above. The wireless communication circuit 52 transitions to a first low power state if it fails to find data in the outbound data buffer 100 of the memory subsystem 54 when a predefined time period elapses since last finding data in the outbound data buffer 100. Thereafter, the wireless communication circuit 52 transitions to successively lower power states as successively longer time periods elapse since last finding data in the outbound data buffer 100. The number of different power states generally range between full (100%) power and a lowest power "deep sleep" state, and may include any number of reduced power states between these two extremes. When in the lowest power "deep sleep" state, the wireless communication circuit 52 periodically, e.g., every 400 milliseconds, wakes up to a "UART only" state, in which the wireless communication circuit 52 has sufficient power to check the status of the outbound data buffer 100 of the memory subsystem 54 via the data UART line. If the outbound data buffer 100 of the memory subsystem 54 has data stored therein, the wireless communication circuit 52 wakes up to a full power state to service the data. If the outbound data buffer 100 of the memory subsystem 54 has no data stored therein, the wireless communication circuit 52 transitions back to the lowest power "deep sleep" state. After being in the lowest power sleep state for a predefined period of time of inactivity, the wireless communication circuit 52 sends a control signal to the power supply 62 that causes the power supply 62 to turn off. As a further example, the wireless communication circuit 52 directly monitors activity of the user buttons 16 via the debounce circuitry 68, and when the wireless communication circuit 52 detects user press of the ON button, the wireless communication processor transitions itself from any of the lower power states to the full power state. Thus, in the lowest power "deep sleep" state, the wireless communication circuit 52 must be capable of monitoring at least the ON button of the user buttons 16. Similarly, when the wireless communication circuit 52 detects user press of the OFF button, the wireless communication circuit 52 transitions itself from any of the power states to the lowest power "deep sleep" state.

When a wireless connection is established between the electronic device 12 and the insulin infusion pump 14, and the UI processor 50 determines that the wireless connection should be terminated, the UI processor 50 stores a message in the outbound data buffer 100 of the memory subsystem 54 that contains a connection termination request. When the wireless communication, circuit 52 thereafter finds the message in the outbound data buffer 100 of the memory subsystem 54, the wireless communication circuit 52 incorporates the message into the predetermined wireless communication protocol and then transmits the message via its wireless communication circuitry to the insulin infusion pump 14. The insulin infusion pump 14 then wirelessly sends a signal containing a predefined connection termination response back to the remote electronic device 12. Subsequently the processor 28 instructs the wireless communication circuit 30 to orderly terminate communications or connections with the wireless communications circuit 52' that may be specific to the predetermined wireless communications protocol. When the wireless connection is terminated in this manner, the wireless communication circuit 52 is operable to periodically, but asynchronously with respect to operation of the UI processor 50, check the outbound data buffer 100 of the memory subsystem 54. If no data resides in the outbound data buffer 100, the wireless communication circuit 52 successively enters lower power sleep states or modes as described above. If, however, the wireless communication circuit 52 finds data in the outbound data buffer 100 of the memory subsystem 54, the wireless communication circuit 52 attempts to establish (or re-establish) a wireless connection with the wireless communication circuit 30 of the insulin infusion pump 14 as described above.

If, after a predefined or programmed number of attempts and/or elapsed time, no wireless connection can be established between the wireless communication circuit 52 and the wireless communication circuit 30, the wireless communication circuit 52 illustratively clears the outbound data buffer 100 of the memory subsystem 54. Alternatively, the UI processor 50 may clear the outbound data buffer 100 if it determines that data exists in the outbound data buffer 100 after some time period has elapsed since storing the wireless communication message in the outbound data, buffer 100 or after some time period has elapsed after determining, based on failure to receive acknowledgements from the insulin infusion pump 14, that a wireless connection between the remote electronic device 12 and the insulin infusion pump 14 no longer exists. In any case, with the outbound data buffer 100 of the memory subsystem 54 empty, the wireless communication circuit 52 successively enters lower power sleep states or modes as described above.

In the event of a lost, wireless connection between the remote electronic device 12 and the insulin infusion pump 14, the wireless communication circuit 52 is operable in one embodiment to turn off its wireless transmission circuitry and to transition to a low power state if it fails to find data in the outbound data buffer 100 of the memory subsystem 54 since last finding data in the outbound data buffer 100. Because the wireless connection is lost, the UI processor 50 will no longer receive acknowledgements from the insulin infusion pump 14 and will therefore cease to store messages in the outbound data buffer 100 of the memory subsystem 54. However, a message, or at least part of a message, may reside within the outbound data buffer 100 when the wireless connection is lost. In this case, after a predefined or programmed number of attempts and/or after a predefined or programmed elapsed time, no wireless connection can be established with the insulin infusion pump 14, the wireless communication circuit 52 illustratively clears the outbound data buffer 100 of the memory subsystem 54. Alternatively, the UI processor 50 may clear the outbound data buffer 100 if it determines that data exists in the outbound data buffer 100 after sometime period has elapsed since last storing a message in the outbound data buffer 100 or after some time period has elapsed after determining, based on failure to receive acknowledgements from the insulin infusion pump 14, that a wireless connection between the devices 12 and 14 no longer exists. In any case, with the outbound data buffer 100 of the memory subsystem 54 empty, the wireless communication circuit 52 successively enters lower power sleep states or modes as described above.

In one illustrative embodiment, the UT processor 50 and the processor 28 of the insulin infusion pump 14 may use scheduled messages and internal timers to control determinations by each of whether a wireless connection between the remote electronic device 50 and the insulin infusion pump 14 exists. For example, during information exchange between the electronic device 12 and the insulin infusion pump 14, the UI processor 50 is operable to periodically, e.g., every 100 milliseconds, transfer a message to the outbound data buffer 100 of the memory subsystem 54 and to reset an internal timer circuit. The wireless communication circuit 52 asynchronously retrieves the message from the outbound data buffer 100 of the memory subsystem 54 and transmits the message to the insulin infusion pump 14 as described above. The insulin infusion pump 14 is responsive to receipt of the message to immediately transmit a message back to the electronic device 12 that contains an acknowledgement. The message transmitted by the insulin infusion pump 14 is received and unpacked from the wireless communication protocol by the wireless communication circuit 52, and then stored by the wireless communication circuit 52 in the inbound data buffer 98 of the memory subsystem 54. The UI processor 50 then retrieves the message from the inbound data buffer 98 of the memory subsystem 54 and, processes the message to determine whether it contains an acknowledgement. As long as an acknowledgement is received by the UI processor 50 in this manner before the next scheduled transfer of a message to the outbound data buffer 100 of the memory subsystem 54, the UI processor 50 resets its internal timer circuit when transferring the next message to the memory subsystem 54. However, if an acknowledgement is not received by the UI processor 50 before the next scheduled transfer of a message to the outbound data buffer 100 of the memory subsystem 54, the UI processor 50 transfers the message to the outbound data buffer 100 of the memory subsystem 54 without resetting its internal timer circuit. If no acknowledgement is received by the UI processor 50 within a predefined or programmed time period, e.g., 1-2 minutes, the internal timer circuit of the UI processor 50 times out and the UI processor 50 stops transferring messages to the outbound data buffer 100 of the memory, subsystem 54. The insulin infusion pump 14, in this embodiment, ceases to send acknowledgements back to the remote electronic device 12 after a predefined or programmed time period, e.g., 2 minutes, has passed without receiving a message transmitted by the electronic device 12.

Illustratively, the UI processor 50 is operable to cease storing messages in the outbound data buffer 100 of the memory subsystem 54 upon detection of insertion of a sample carrier 22 into the carrier port 20 as described above. After a predefined time period in which the wireless communication circuit 52 thereafter fails to find such messages in the outbound data buffer 100 of the memory subsystem 54, the wireless communication circuit 52 begins transitioning to lower power states as described above. When the UI processor 50 then resumes storing messages in the outbound data buffer 100 of the memory subsystem 54 after the analyte measurement is complete, the wireless communication circuit 52 wakes up to full power to service it. This may take at least a wake up time period, e.g., as much as 400 milliseconds, if the wireless communication circuit 52 has just entered the lowest power "deep sleep" state when the first message is stored in the outbound data buffer 100 of the memory subsystem 54 after the analyte measurement is complete.

Unless the remote electronic devices 12 and the insulin infusion pump 14 are communicating information, the wireless communication circuit 52 is generally in one of the lower power sleep states or modes. When insertion of a sample carrier 22 into the carrier port 20 is detected, the electronic device 12 performs an analyte determination test as described above. The electronic device 12 generally does not wirelessly communicate with the insulin infusion pump 14 during the analyte determination test, and the wireless communication circuit 52 is thus typically in one of the lower power sleep states when insertion of the sample carrier 22 into the carrier port 20 is detected. Because the UI processor 50 stops storing messages in the outbound data buffer 100 of the memory subsystem 54 when insertion of the sample carrier 22 into the carrier port 20 is detected, the wireless communication circuit 52 therefore typically enters successively lower power sleep states after insertion of the sample carrier 22 into the carrier port 20 is detected.

While the electronic device 12 is illustrated and described above with respect to FIGS. 1-3 as including an analyte measuring facility 88, such an analyte measuring facility may be omitted in alternative embodiments. In any case, the electronic device 12 and the insulin infusion pump 14 may illustratively be paired according to a pairing process that establishes secure communications between the electronic device 12 and the insulin infusion pump 14. Illustratively, this process may be carried out to initially establish secure wireless communications between the electronic device 12 and a particular insulin infusion pump 14, and then again if the electronic device 12 is to be paired with a different insulin infusion pump 14 or vice versa. In one illustrative embodiment, the electronic device 12 may only be paired with a single insulin infusion pump 14 at a time, although this disclosure contemplates other embodiments in which the electronic device 12 may be paired with any number of medical devices 14 generally and/or other electronic devices, and/or in which the medical device 14 may be paired with any number of electronic devices 12 or other medical devices. In any case, further details relating to one illustrative pairing and authentication process are provided in co-pending PCT Patent Application No. PCT/US2008/066247, entitled METHOD FOR PAIRING AND AUTHENTICATING ONE OR MORE MEDICAL DEVICES AND ONE OR MORE REMOTE ELECTRONIC DEVICES, the disclosure of which has, been incorporated herein by reference.

Figure 4:
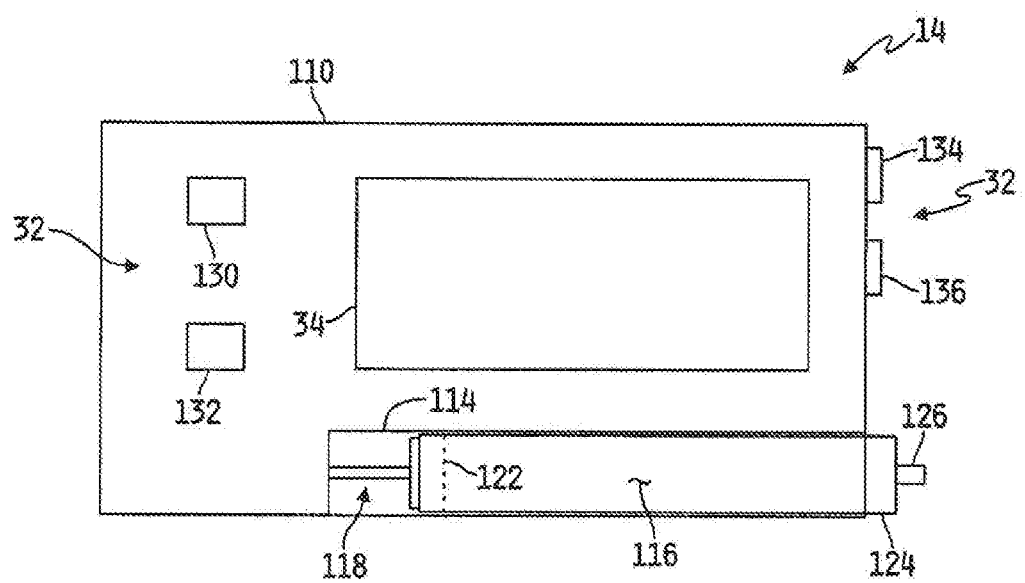
FIG. 4 shows a diagram of one illustrative embodiment of the medical device of FIG. 1 provided in the form of a liquid infusion pump.

Referring now to FIG. 4, a diagram is shown of one illustrative embodiment of the medical device 14 provided in the form of a liquid infusion pump. In the illustrated embodiment, the pump 14 has a housing 110 that carries the user keys 32 and the display device 34. The housing 110 illustratively defines a liquid cartridge chamber 114 that is sized to hold a cartridge 116 of liquid, e.g., a drug, to be infused by the pump 14 into a body. A pump motor (not shown) is configured to control a conventional drive mechanism 118 that is configured to engage a plug 122 defined at one end of a liquid cartridge 116. The plug 122 forms a movable liquid seal with the liquid cartridge 116, and the drive mechanism 118 moves the plug 122 relative to the liquid cartridge 116 under control of the pump motor to dispense liquid from the liquid cartridge 116 in a conventional manner. The opposite end of the liquid cartridge 116 is secured to the housing 110 via releasably engageable adapter 124 through which a conventional Luer lock fitting 126 extends. The Luer lock fitting 126 is configured to be fluidly connected to an infusion set (not shown) that is configured to extend subcutaneously into a body of a user. Under the control of the processor 28 in a conventional manner, the pump motor controllably advances the drive mechanism 118 into the liquid cartridge 116 and thereby force liquid from the cartridge 116 into the body of the user via the Luer lock fitting 126 and subcutaneous infusion set. The user keys 32 of the liquid infusion pump 14 are illustratively distributed in groups of two buttons or keys 130, 132 and 134, 136 each near opposite sides of the display unit 34. In the illustrated embodiment, the key 130 is a MENU key, the key 132 is an "OK" key, the key 134 is an up key and the key 136 is a down key. The MENU key 130 allows the user to select a desired menu from a group of menus, the OK key 132 allows the user to select menu options and to select programming parameters, and the up and down keys 134, 136 provide for up and down navigation respectively through application screens displayed on the display unit 34. By simultaneously pressing the MENU key 130 and the up key 134, the user can sequentially navigate back through the previous menus.

Figure 5:
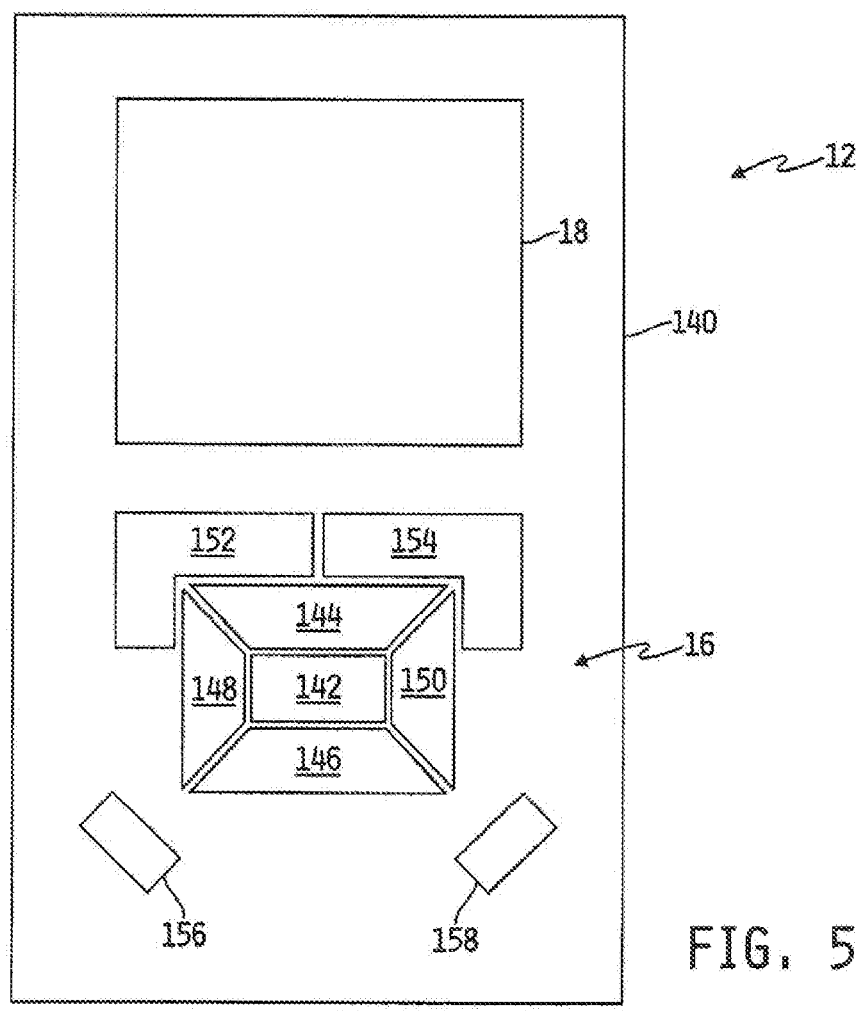
FIG. 5 shows a diagram of one illustrative embodiment of the exterior of the remote electronic device.

Referring now to FIG. 5, a diagram is shown of one illustrative embodiment of the exterior of the remote electronic device 12. In the illustrated embodiment, the remote electronic device 12 includes a housing 140 that carries the display device 18 and the user buttons 16. In the embodiment illustrated in FIG. 5, the user buttons 16 include an ENTER key 142, an up key 144, a down key 146, a left key 148 and a right key 150, wherein the keys 144, 146, 148 and 150 are configured to provide for up, down, left and right navigation respectively through application screens displayed on the display device 18. The user buttons 16 further include two so-called "soft" keys 152 and 154 that may be programmed to provide desired functions, as well as an on/off button 156 and a display backlight activation button 158.

The memory 72 connected to the UI processor 50 of the remote electronic device 12 (see FIG. 2) has instructions stored therein that are executable by the UI processor 50 to operate the remote electronic device 12 in a remote terminal mode in which the remote electronic device 12 is configured to operate, substantially in real time, the liquid infusion pump 14. Illustratively, this is accomplished by periodically transferring to the remote electronic device 12, by the processor 28 via the wireless communication circuit 30, screen data that corresponds to what the processor 28 would normally display on the display device 34 of the pump 14 if the pump 14 was being operated locally under the control of the processor 28 and not being remotely controlled by the remote electronic device 12. At least some of the user keys 32 of the liquid infusion pump 14 are emulated on the remote electronic device 12 with selected ones of the user buttons 16, and the selected ones of the user buttons 16 of the remote electronic device 12 are then used to navigate the transferred screen on the display 18 of the remote electronic device just as a user of the liquid infusion pump 14 would navigate the screen displayed on the display device 34 of the pump 14 using the pump keys 32. Each button press on the remote electronic device 12 is wirelessly transmitted to the infusion pump 14, and upon receiving the button press the pump 14 processes the wirelessly received button press just as if it had received the button press locally from a corresponding one of the pump keys 32. If the button press on the remote electronic device 12 results in a change in the pump screen displayed on the display device 34, the pump 14 wirelessly transfers new screen information to the remote electronic device 12 for display on the display device 18 of the remote electronic device 12.

Referring now to FIG. 6, a table is shown of one illustrative map for relating the user keys 32 of the liquid infusion pump 14 to user buttons 16 of the remote electronic device 12 during the remote terminal operating mode. As illustrated in FIG. 6, during the remote terminal operating mode the up button 144 of the remote electronic device 12 corresponds to the up button 134 of the liquid infusion pump 14, the down button 146 corresponds to the down button 136, the left button 148 of the remote electronic device 12 corresponds to the MENU button 130 of the liquid infusion pump 14 and the right button 150 corresponds to the "OK" or check button 132. The right soft key 154 illustratively corresponds to a simultaneous press of the menu key 130 and the up key 134 which allows for sequential back navigation through previous menus. The left soft key 152 returns the display to the main pump menu, and a simultaneous press of the up and left buttons 144 and 148 corresponds to a simultaneous press of the menu and up keys 130 and 134 which allows for sequential back navigation through previous menus as just described. As will be shown by example hereinafter, the UI processor 50 is operable in the remote terminal mode to control the display device 18 of the remote electronic device 12 to always display at least a portion of the map illustrated in FIG. 6 as a guide to users attempting to navigate the transferred pump screen being displayed on the display device 18 of the remote electronic device 12.

Figure 7:
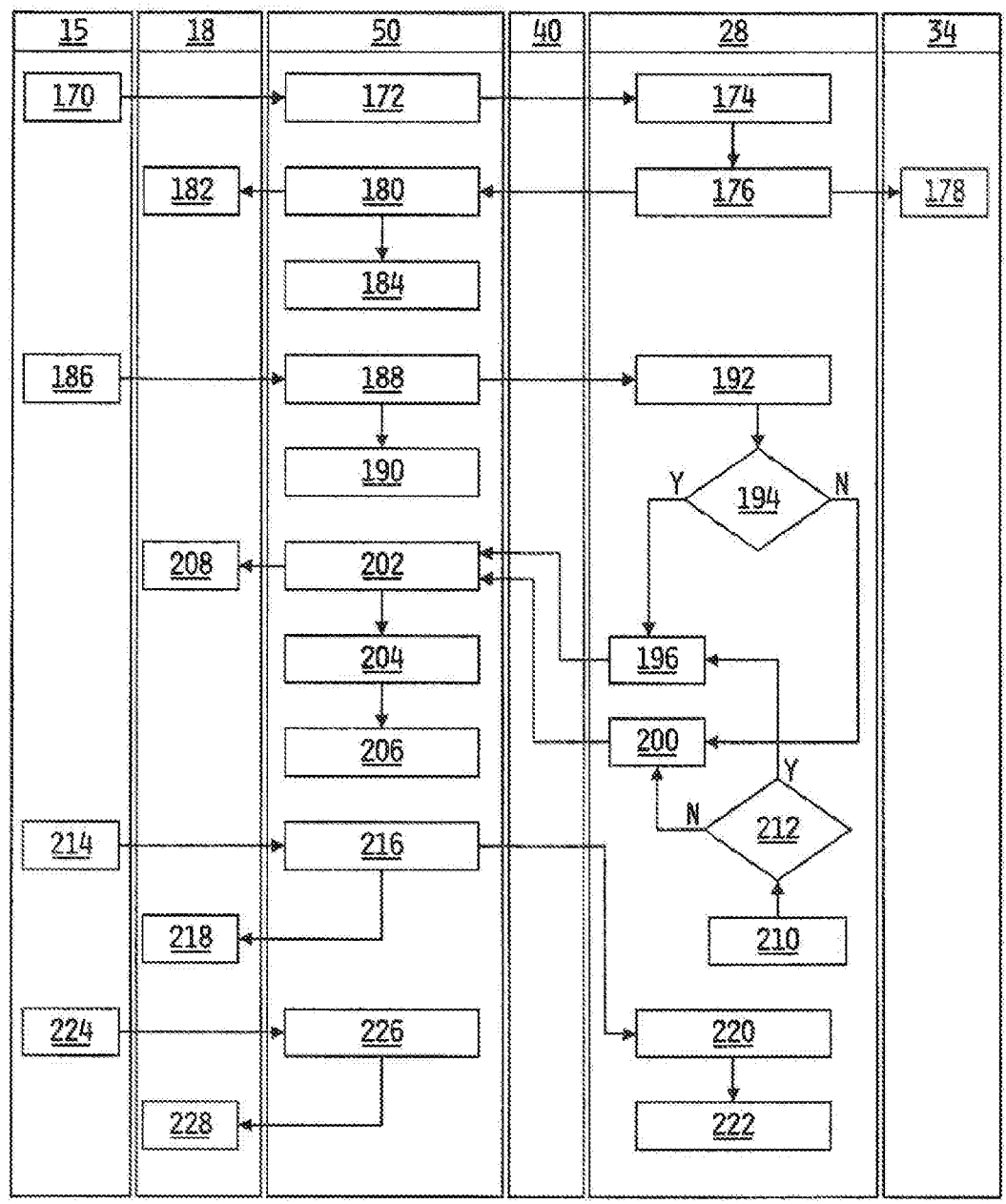
FIG. 7 shows, a flowchart of one illustrative embodiment of a process for carrying out the remote terminal operating mode of the liquid infusion pump via the remote electronic device.

Referring now to FIG. 7, a flowchart is shown of one illustrative process for carrying out the remote terminal operating mode of the liquid infusion pump 14 via the remote electronic device 12. The flowchart of FIG. 7 is partitioned into the various entities and device/electrical components that carry out the various acts of the remote terminal operating mode process. Thus, for example, a person 15 conducting the remote terminal operating mode process will carry out some of the acts, the display device 18 of the remote electronic device 12 will carry out some of the acts, the UI processor 50 of the remote electronic device 12 will carry out some of the acts, the processor 28 of the liquid infusion pump 14 will carry out some of the acts and the display device 34 of the liquid infusion pump 14 will carry out some of the act. Item 40 corresponds to the wireless communication link, that has been established between the medical device 14 and the remote electronic device 12. To the extent that the illustrated process operates in the remote electronic device 12, this portion of the process is illustratively stored in the memory device 66 in the form of instructions that are executable by the UI processor 50 to carry out the illustrated process. Likewise, to the extent that the illustrated process operates in the liquid infusion pump 14, this portion of the process is illustratively stored in the memory device 25 in the form of instructions that are executable by the processor 28 to carry out the illustrated process.

Illustratively, a precondition for the remote terminal operating mode process of FIG. 7 is that the wireless communication link 40 has been established between the remote electronic device 12 and the liquid infusion pump 14, and that a menu and/or user button is available to the user 15 that the user may select to enter the remote terminal operating Mode. The process begins at step 170 where the user 15 selects the button and/or appropriate menu item displayed on the display unit 18 to start the remote terminal operating mode. Thereafter at step 172 the UI processor 50 initiates the remote terminal mode within the remote electronic device 12 and sends via the wireless communication circuit 52 a remote terminal mode start command to the infusion pump 14. In one embodiment, the UI processor 50 is operable to initiate the remote terminal mode within the remote electronic device at step 172 by redefining at least some of the plurality of the user buttons 16, e.g., as illustrated in FIG. 6, to emulate at least some of the user keys 32 of the pump 14 using selected ones of the user buttons 16 on the remote electronic device 12. In an alternative embodiment, the infusion pump 14 may be configured to send user key emulation information wirelessly to the remote electronic device 12. In any case, the infusion pump 14 at step 174 receives via the wireless communication circuit 30 the remote terminal mode start command from the remote electronic device 12, and, thereafter at step 176 the processor 28 is operable to transmit via the wireless communication module 30 screen data that is generated by the processor 28 for display on the display device 34 and that corresponds to a screen that the processor 28 would currently be displaying on the display device 34 if the infusion pump 14 was operating in a local operating mode, i.e., not operating in the remote terminal operating mode. Illustratively, the processor 28 may also send alert data along with the screen data. The alert data may illustratively include audible and/or vibratory device commands produced by the processor 28 to activate the corresponding audible and/or vibratory devices 36 and 38 respectively and/or one or more message commands produced by the processor 28 to display a corresponding one or more messages, although this disclosure contemplates other embodiments in which the alert data may include more, less and/or different information relating to the pump 14.

In one embodiment, the screen data transmitted by the processor 28 via the wireless communication circuit 30 at step 176 comprises bit map data, e.g. pixels, which the processor 28 illustratively sends, via the wireless communication circuit 30, to the remote electronic device 12 in four consecutive messages. In this embodiment, the screen image displayed on the display device 34 of the infusion pump 14 is illustratively partitioned into four consecutive image rows, and the bit map data in each of the four messages illustratively comprises one fourth of the total displayed image. In alternative embodiments, the bit map may be partitioned into more or fewer rows, and sent to the remote electronic device in more or fewer messages, or may alternatively be partitioned into any number of columns, parts of rows and/or columns, raster patterns or other image segments or blocks and transmitted to the remote electronic device in any number of consecutive messages.

Step 176 advances to step 178 where the processor 28 is further responsive to the remote terminal mode start command to control the display unit 34 to display a predefined screen. In one embodiment, the processor 28 is operable at step 178 to control the display unit 34 to display an indicator of the wireless communication link 40 as long as the wireless communication link 40 is established during the remote terminal operating mode. In embodiments in which the wireless communication protocol used between the two devices 12 and 14 is the BlueTooth® communications protocol, the indicator of the wireless communication link 40 may be, for example, a conventional BlueTooth® symbol, i.e., a predefined symbol that is generally recognized as identifying BlueTooth® communications. In alternative embodiments, the processor 28 may be operable at step 178 control the display device 34 to display one or more other indicators that the wireless communications link 40 is established or to display other information.

Step 176 also advances to step 180 where the UI processor 50 receives, via the wireless communication circuit 54, the screen data (and any alert data) sent by the infusion pump 14. Thereafter at step 182, the UI processor 50 is responsive to the screen data sent by the infusion pump 14 to control the display device 18 according to the received screen data to display on the display device 18 the screen that the processor 28 would currently be displaying on the display device 34 if the infusion pump 14 was not operating in the remote terminal operating mode.

The UI processor 50 is further operable at step 182 to control the display 18 to display navigation thereon by the selected ones of the plurality of user buttons 16 and to display user selection of items on the display device 18. Illustratively, the UI processor 50 is further operable at step 182 to control the display device 18 to display a map that relates emulated ones of the user keys 32 of the infusion pump 14 to selected ones of the user buttons 16 of the remote electronic device 12. This latter feature is illustrated by example in FIG. 8.

The process also advances from step 180 to step 184 where the UI processor 50 is responsive to any alert data that was sent by the pump 14 along with the screen data to activate the audible indicator 72 and/or the vibratory device 74 if the alert data includes audible and/or vibratory device commands, and/or to control the display device 18 to display a suitable message if the alert data includes message data.

With the remote terminal operating mode established, the user buttons 16 of the remote electronic device 12 can be manipulated to navigate the screen displayed on the display device 18. The user can select pump commands from the pump screen displayed on the display device 18, and the selected pump commands are then wirelessly transmitted to the infusion pump 14 to be acted on in the same way as would occur if the pump commands were received locally at the pump 14, i.e., via the pump keys 32. This part of the process is illustrated in FIG. 7 beginning at step 186 where the user 15 selects, i.e., presses, one or a simultaneous combination of the user buttons 16. Thereafter at step 188 the UI processor 50 sends the selected user button command to the infusion pump 14 via the wireless communication circuit 52. Following step 188, the process advances to step 190 where the UI processor 50 disregards any further user button commands until an acknowledgement is received from the infusion pump 14 that the button command sent at step 188 was received and acted upon by the pump 14. Step 188 also advances to step 192 where the processor 28 of the pump 14 receives, via the wireless communication circuit 30, and acts upon the user button command sent by the remote electronic device 12. The user button command may correspond to a cursor move, a menu command, an OK or check command or other command. Some user button commands will result in a change of state of the infusion pump 14 and/or a change in the screen that would be displayed on the display device 34 of the pump 14 by the processor 28 if the pump 14 was not currently in the remote command mode.

The process advances from step 192 to step 194 where the processor 28 determines whether the user button command sent by the remote electronic device 12 at step 188 is one that would have resulted in a change in the screen displayed on the display device 34 of the infusion pump 14 if the pump 14 was not currently in the remote terminal mode. If so, the process advances to step 196 where the processor 28 sends updated screen data, corresponding to an updated screen that would be displayed by the processor 28 on the display device 34 in response to the user button command if the pump was not currently in the remote terminal operating mode, along with any alert data, to the remote electronic device 12 via the wireless communication circuit 30. If, at step 194, the processor 28 determines that the user button command received at step 192 would not have resulted in a change of the screen displayed by the processor 28 on the display device 34 if the infusion pump 14 was not currently in the remote terminal operating mode, the process advances to step 200 where the processor 28 sends a key acknowledgement, corresponding to an acknowledgement that the user button command sent by the remote electronic device 12 at step 188 was received by the processor 28, along with alert data, to the remote electronic device 12 via the wireless communication circuit 30.

At step 202, the UI processor 50 receives either the updated screen data generated by the processor 28 at step 196 or the key acknowledgement generated by the processor 28 at step 200, along with alert data, via the wireless communication circuit 52. The UI processor 50 is responsive to the alert data received from the pump 14 at step 188 to control the audible indication device 72 and/or the vibration device 74 to notify the user of the remote electronic device 12 that the user button selection made at step 186 is acknowledged. If updated screen data was received from the infusion pump 14 at step 202, the UI processor 50 is responsive to the received updated screen data to control at step 208 the display device 18 according to the updated screen data to display on the display device 18 the screen that the processor 28 would currently be displaying on the display device 34 if the infusion pump 14 was not operating in the remote terminal operating mode. If no updated screen data was received at step 202, step 208 is not executed.

The process also advances from step 202 to step 204 where the UI processor 50 is further responsive to the alert data to activate the audible indicator 72 and/or the vibratory device 74 if the alert data includes audible and/or vibratory device commands in addition to those used to acknowledge the user button command made at step 186, and/or to control the display device 18 to display a suitable message if the alert data includes message data. Thereafter at step 206, the UI processor 50 accepts new user button commands, i.e., acts upon user press of a new one or simultaneous combination of the user buttons 16.

One or more operating events of the infusion pump 14 may also result in a condition in which the processor 28 of the pump 14 would normally have controlled the display device 34 to display updated screen data if the pump 14 was not currently operating in the remote terminal mode. In such cases, the screen displayed by the UI processor 50 on the display device 18 of the remote electronic device 12 must then be updated to accurately reflect the current operating conditions of the pump 14. This process is illustrated at step 210 where a pump operating event occurs. Thereafter at step 212, the processor 28 of the pump 14 determines whether the pump operating event that occurred at step 210 would normally have caused the processor 28 to update the screen displayed on the display device 34 if the pump 14 was not currently in the remote terminal operating mode. If so, the process advances to step 196 where the processor 28 sends the updated screen data, along with alert data, to the remote electronic device via the wireless communication circuit 30 as described above. If, at step 212, the processor 28 determines that the pump event detected at step 210 would not normally have caused the processor 28 to update the screen displayed on the display device 34 if the pump 14 was not currently in the remote terminal operating mode, the process advance to step 200 where the processor 28 sends only alert data, if any, to the remote electronic device 12 via the wireless communication circuit 30.

At some point, the user 15 may wish to exit the remote terminal operating mode. This part of the process is illustrated in FIG. 7 beginning with step 214 where the user selects one of the user buttons 16, e.g., the soft key 152 as illustrated in FIG. 6, to exit the remote terminal operating mode. Thereafter at step 216, the UI processor 50 illustratively exits the remote terminal operating mode by resetting the user buttons 16 to their default functions and by transmitting, via the wireless communication circuit 52, a remote terminal mode stop command. The UI processor 50 is also operable at step 216 to advance to step 218 where the UI processor 50 controls the display device 18 to display a main menu or other suitable menu. The processor also advances from step 216 to step 220 where the processor 28 of the infusion pump 14 receives, via the wireless communication circuit 30, the remote terminal mode stop command. Upon receiving the remote terminal stop command, the processor 28 exits the remote terminal operating mode and illustratively continues thereafter to operate in accordance with any commands previously received from the remote electronic device 12 until such time that a user commands the pump 14 locally via the user keys 32 or a new remote terminal operating mode session is initiated by the remote electronic device 12. From step 220, the process illustratively advances to step 222 where the processor 28 is illustratively operable to transfer pump operating history and current time/date information to the remote electronic device 12.

In one illustrative embodiment, the UI processor 50 does not acknowledge attempts to power down the remote electronic device 12 while in the remote terminal operating mode. In alternate embodiments, this feature is omitted. In embodiments that do include this feature, a process for carrying out this feature, is illustrated in FIG. 7 beginning with step 224 where the user 15 presses the power off button, e.g., the power button 156 on the remote electronic device 12 illustrated in FIG. 5. Thereafter at step 226, the UI processor 50 does not act on the power down request and instead advances to step 228 where the UI processor 50 controls the display device 18 to display a message to the user indicating that the remote electronic device 12 cannot be turned off in the remote terminal operating mode.

Figure 8:
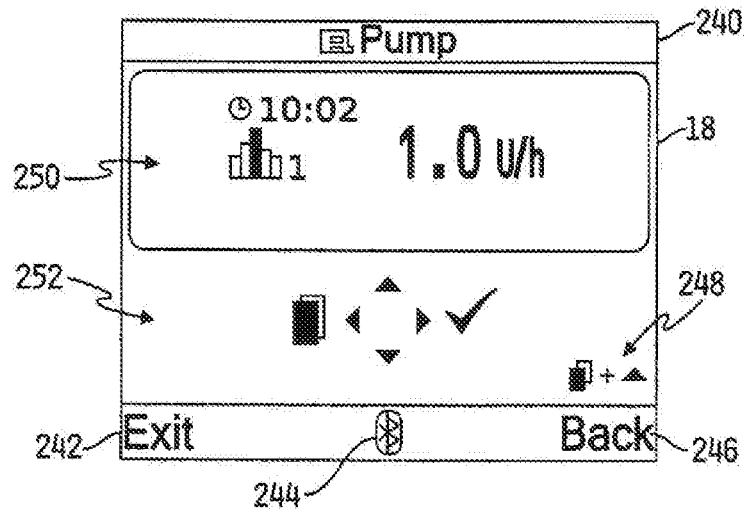
FIG. 8 shows a graphic representation illustrating an example infusion pump display screen displayed on the display unit of the remote electronic device.

Referring now to FIG. 8, an example screen 240 that is displayed on the display device 18 of the remote electronic device 12 during the remote terminal operating mode is shown. In the illustrated example, the screen 240 includes an EXIT indicator 242 that may be selected, e.g., via the soft key 152, to exit the remote terminal operating mode as described above. The screen 240 also includes a wireless connection indicator 244 to indicate to the user the status of the wireless connection 40 between the remote electronic device 12 and the liquid infusion pump 14. To the right of the wireless connection indicator 244 is a Back indicator 246 that may be selected, e.g., via the soft key 154 or by the simultaneous combination of the up and left buttons 144 and 148 respectively, to navigate to a previously displayed screen. Illustratively, the combination 248 of user keys 32 on the pump 14 that would be required to navigate to a previous screen if the screen was displayed on the display device 34 of the pump 14 is displayed above the Back indicator 246. The pump screen information 250 is also displayed on the screen 240 where the pump screen information 250 is identical to which would be displayed on the display device 28 of the pump 14 if the pump 14 was not operating in the remote terminal operating mode. Below the pump screen information 250 a key/button map 252 is shown, as described briefly hereinabove, that relates the keys 130, 132, 134 and 136 of the user keys 32 of the infusion pump 14 to corresponding buttons of the user buttons 16 on the remote electronic device 12 when operating in the remote terminal mode. Thus, for example, the map 252 indicates that the up and down functions correspond to the same keys/buttons on both devices 12 and 14, whereas the MENU key 130 of the pump 14 corresponds to the left button 148 of the remote electronic device 12 (see also FIG. 6). Similarly, the map 252 indicates that the OK or check key 132 of the pump 14 corresponds to the right button 150 of the remote electronic device 12. It will be understood that the screen 240 may be differently arranged to include more or fewer display items and/or to show the displayed items in a different form, and that any such different arrangements of the screen 240 are contemplated by this disclosure.

It is possible during the remote terminal operating mode that a user may not activate, i.e., press, any of the user buttons 16 of the remote electronic device 12 for a prolong time period, and that the pump 14 similarly may not undergo a pump event that results in a change to the screen displayed on the display device 18 of the remote electronic device 12 for a prolonged time period. Referring now to FIGS. 9A and 9B, two flowcharts are shown of one illustrative embodiment of processes 260 and 280 respectively for maintaining the liquid infusion pump 14 and the remote electronic device 12 wirelessly connected during such conditions that may be encountered during the remote terminal operating mode. The processes 260 and 280 presume that the wireless communication link 40 is and remains established.

Each of the UI processor 50 of the remote electronic device 12 and the processor 28 of the liquid infusion pump 14 includes an alive message timer and an alive message received timer, the operation of which will be described with respect to the processes 260 and 280 of FIGS. 9A and 9B respectively. Illustratively, each of the processes 260 and 280 are stored in the memory devices 66 and 25 of the devices 12 and 14 respectively in the form of instructions that are executable by the processors 50 and 28 respectively to carry out the alive timer function. The steps of the processes 260 and 280 will first be generally described, and then operation of the processes 260 and 280 from the perspective of the remote electronic device 12 and from the perspective of the liquid infusion pump 14 will then be described.

Referring to FIG. 9A, the process 260 begins at step 262 where the processor 50, 28 determines whether the corresponding device 12, 14 has entered the remote terminal operation mode, e.g., as described hereinabove with respect to FIG. 7. If not, the process 260 loops back to the beginning of step 262. If the processor 50, 28 determines at step 262 that the device 12, 14 has entered the remote terminal mode, the processor 50, 28 is operable at step 264 to reset an internal alive message timer. Thereafter at step 264, the processor 50, 28 is operable to determine whether a wireless message has been sent by one of the devices 12, 14 to the other device 14, 12.

When being executed by the processor 28 of the liquid infusion pump 14, the processor 28 is illustratively operable at step 266 to determine whether a message that includes updated screen data and alert data or a user button acknowledgement and alert data has been wirelessly sent by the liquid infusion pump 14 via the wireless communication circuit 30. When being executed by the UI processor 50 of the remote electronic device 12, the UI processor 50 is illustratively operable at step 266 to determine whether a message that includes a user button command has been wirelessly sent by the electronic device 12. Illustratively, the UI processor 50 is operable to determine that a message that includes a user button command has been sent by the electronic device 12 when the UI processor stores the user button command in the outbound buffer 100 of the memory subsystem 54 as described hereinabove. As also described hereinabove, the UI processor 50 does not control the operation of the wireless communication circuit 52 and therefore the UI processor 50 has no knowledge, at least until receiving confirmation from the infusion pump 14, that the message containing the user button command is actually wirelessly transmitted by the wireless communication circuit 52.

In any case, if the processor 50, 28 determines at step 266 that a message has been sent by the device 12, 14 respectively to the other device 14, 12 respectively, the process 260 loops back to step 264 to reset the alive message timer that is illustratively internal to the processor 50, 28. If the processor 50, 28 instead determines at step 266 that a message has not been sent by the device 12, 14 to the other device 14, 12, the process 260 advances to step 268 where the processor 50, 28 is operable to determine whether the alive message timer has timed out. If not, the process 260 loops back to the beginning of step 266. If, at step 268, the processor 50, 28 determines that the alive message timer has timed out, the processor 50, 28 is operable to send, via the wireless communication circuit 52, 30, an alive message to the other device 14, 12 respectively.

Referring now to FIG. 9B, the process 280 begins at step 282 where the processor 50, 28 determines whether the corresponding device 12, 14 has entered the remote terminal operation mode, e.g., as described hereinabove with respect to FIG. 7. If not, the process 280 loops back to the beginning of step 282. If the processor 50, 28 determines at step 282 that the device 12, 14 has entered the remote terminal mode, the processor 50, 28 is operable at step 284 to reset an internal alive message (AM) received timer. Thereafter at step 284, the processor 50, 28 is operable to determine whether a wireless message has been received by the corresponding device 12, 14 from the other device 14, 12.

When being executed by the processor 28 of the liquid infusion pump 14, the processor 28 is illustratively operable at step 286 to determine whether a message has been received by the wireless communication circuit 30 that includes a user button command sent by the wireless communication device 12. When being executed by the UI processor 50 of the remote electronic device 12, the UI processor 50 is illustratively operable at step 286 to determine whether a message has been received by the wireless communication circuit 52 that includes updated screen data and alert data or a user button acknowledgement and alert data. In any case, if the processor 50, 28 determines at step 286 that a message has been received by the device 12, 14 respectively from the other device 14, 12 respectively, the process 280 loops back to step 284 to reset the alive message received timer that is illustratively internal to the processor 50, 28. If the processor 50, 28 instead determines at step 286 that a message has not been received by the device 12, 14 from the other device 14, 12, the process 280 advances to step 288 where the processor 50, 28 is operable to determine whether the alive message received timer has timed out. If not, the process 280 loops back to the beginning of step 286. If, at step 288, the processor 50, 28 determines that the alive message received timer has timed out, the processor 50, 28 is operable to exit the remote terminal mode.

As described above, versions of each of the processes 260 and 280 are executed by the UI processor 50 of the remote electronic device and also by the processor 28 of the liquid infusion pump 14. Illustratively, the alive message timer is configured in the UI processor 50 to time out after a time period T1, and the alive message received timer is configured in the UI processor 50 to time out after a time period T2, where T2>T1. Further illustratively, the alive message timer is configured in the processor 28 to time out after a time period T3, and the alive message received timer is configured in the processor 28 to time out after a time period T4, where T4>T3. In one embodiment, T1=T3 and T2=T4, although in alternate embodiments T1≠T3 and/or T2≠T4. In one specific embodiment, T1=T3=approximately 1.5 seconds, and T2=T4=approximately 2 seconds, although other values of T1=T4 may alternatively be used.

From the perspective of the remote electronic device 12, the UI processor 50 is operable in the process 260 to reset the alive message timer that is internal to the UI processor 50 each time that the UI processor 50 stores a user button command in the outbound buffer 100 of the memory subsystem 54. In the meantime, the processor 28 of the liquid infusion pump 14 is operable in the process 280 to reset the alive message received timer that is internal to the processor 28 each time that the processor 28 receives, via the wireless communication circuit 30, a user button command from the remote electronic device 12. If the UI processor 50 determines at any time that the alive message timer times out following the storage of the most recent user button command in the outbound buffer 100, the UI processor 50 sends, via the wireless communication circuit 52, an alive message to the liquid infusion pump 14. Meanwhile; the processor 28 of the pump 14 has not received any user button commands for at least the time out time period of the alive message timer, and the processor 28 is therefore continually executing steps 286 and 288. When the processor 28 then receives the alive message sent by the remote electronic device 12, the alive message received timer internal to the processor 28 has not yet timed out, and the process 280 then follows the "YES" branch of step 286 where the alive message received timer is reset. As long as the wireless communication link 40 exists between the two devices 12, 14 and the time out period of the alive message received timer in the processor 28 is sufficiently greater than the time out period of the alive message timer in the processor 50 so that the processor 28 has adequate time to reset the alive message received timer after receiving the alive message from the remote electronic device 12, the remote terminal operating mode is maintained. Illustratively, the processes 260 and 280 are repeatedly executed by the UI processor 50 and the processor 28 respectively as long as the remote terminal operating mode is active.

From the perspective of the liquid infusion pump 14, the processor 28 is operable in the process 260 to reset the alive message timer that is internal to the processor 28 each time that the processor 28 sends, via the wireless communication circuit 30, updated screen data and alert data or a user button acknowledgement and alert data to the remote electronic device 12. In the meantime, the UI processor 50 of the remote electronic device 12 is operable in the process 280 to reset the alive message received timer that is internal to the UI processor 50 each time that the UI processor 50 receives, via the wireless communication circuit 52, the updated screen data and alert data or a user button acknowledgement and alert data from the infusion pump 14. If the processor 28 determines at any time that the alive message timer times out following sending of the most recent updated screen data and alert data or a user button acknowledgement and alert data, the processor 28 sends, via the wireless communication circuit 30, an alive message to the remote electronic device 12. Meanwhile, the UI processor 50 of the remote electronic device 12 has not received any updated screen data and alert data or a user button acknowledgement and alert data for at least the time out time period of the alive message timer, and the UI processor 50 is therefore continually executing steps 286 and 288. When the UI processor 50 then receives the alive message sent by the infusion pump 14, the alive message received timer internal to the UI processor 50 has not yet timed out, and the process 280 then follows the "YES" branch of step 286 where the alive message received timer is reset. As long as the wireless communication link 40 exists between the two devices 12, 14 and the time out period of the alive message received timer in the UI processor 50 is sufficiently greater than the time out period of the alive message timer in the processor 28 so that the UI processor 50 has adequate time to reset the alive message received timer after receiving the alive message from the liquid infusion pump 14, the remote terminal operating mode is maintained.

If step 290 is reached by either processor 50, 28, the processor 50, 28 is operable to exit the remote terminal mode. Step 290 will illustratively be reached by either, or both of the processor 28 and the processor 50 if the wireless communication link 40 is lost or becomes corrupted. In such cases, the processor 50 is operable as described with respect to the process illustrated in FIG. 7 to exit the remote terminal operating mode. The processor 28 is likewise operable in such cases to exit the remote terminal operating mode, but may not be operable as described with respect to FIG. 7 to transfer any pump history and/or time/date information to the remote electronic device. In such cases, the pump 14 will illustratively be operable to transfer pump history and time/date information to the remote electronic device 12 when a wireless communication link 40 is next established between the devices 12 and 14. Illustratively, the processes 260 and 280 are repeatedly executed by the processor 28 and the UI processor 50 respectively as long as the remote terminal operating mode is active.

Figure 10:
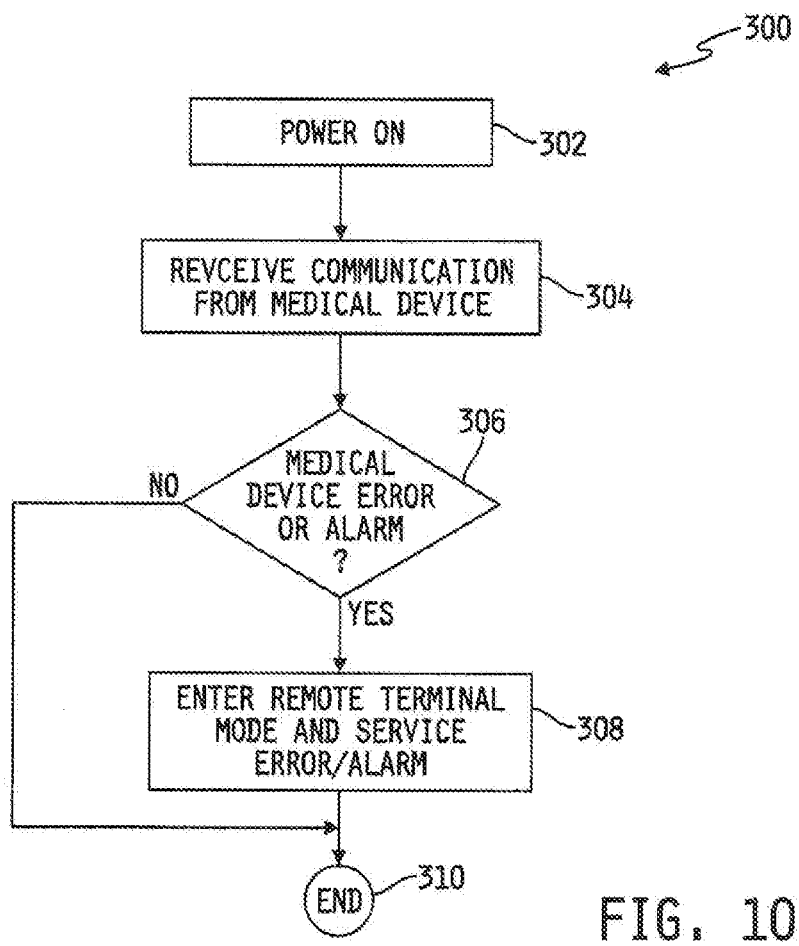
FIG. 10 shows a flowchart of one illustrative embodiment of a process for automatically entering the remote terminal operating mode under certain system operating conditions.

During operation of the pump 14 in operating modes other than the remote terminal operating mode, the remote electronic device 12 may be in a powered off mode. If an error or alarm condition then occurs on the liquid infusion pump 14 and the remote electronic device 12 is thereafter powered up, the remote electronic device 12 illustratively enters the remote terminal mode automatically. Referring to FIG. 10, a flowchart is shown of one illustrative embodiment of such a process 300 for automatically entering the remote terminal operating mode under the conditions just described. The process 300 is illustratively stored in the memory device 66 in the form of instructions that are executable by the UI processor 50 to carry out the process 300. The process 300 presumes that the remote electronic device 12 is initially powered down and the liquid infusion pump 14 develops an error or alarm condition. The process 300 begins at step 302 where the remote electronic device 12 is manually powered on, e.g., by user activation of the on/off button 156. Thereafter at step 304 the remote electronic device 12 receives a wireless message from the pump 14. Thereafter at step 306, the UI processor 50 determines from the message whether the pump 14 currently has an error or alarm condition. If so, the UI processor 50 automatically enters the remote terminal operating mode at step 308, such as by following the process illustrated from steps 172-182 of FIG. 7. From step 308 and from the NO branch of step 306, the process 300 ends at 310.

Figure 11:
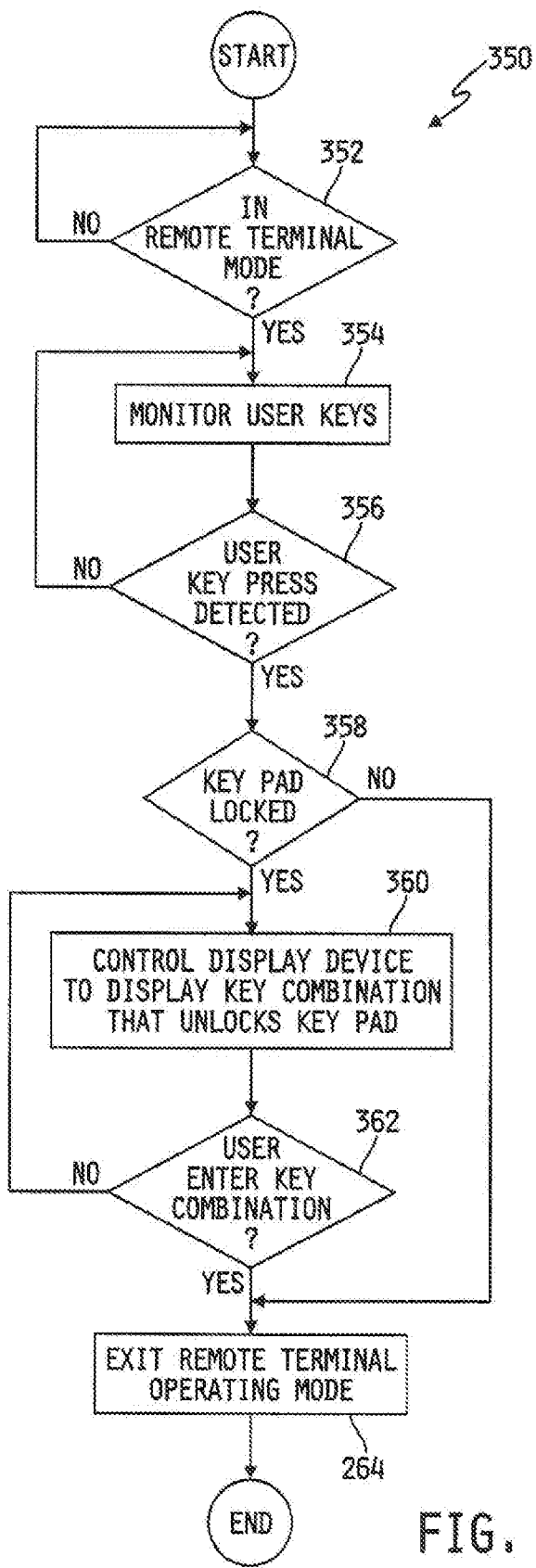
FIG. 11 shows a flowchart of one illustrative embodiment of a process that operates on the liquid infusion pump to exit the remote terminal operating mode using the key pad of the liquid infusion pump.

While operating in the remote terminal mode as described herein, the processor 28 of the liquid infusion pump 14 is operable in one embodiment to monitor the user keys 32 and to exit the remote terminal operating mode upon detection of a user press of one of the user keys 32. Referring to FIG. 11, a flowchart is shown of one illustrative embodiment of such a process 350 for monitoring the user keys 32. The process 350 is illustratively stored in the memory device 25 in the form of instructions that are executable by the processor 28 to carry out the process 350. In the illustrated embodiment, the process 350 begins at step 352 where the processor 28 determines whether the pump 14 is currently in the remote terminal operating mode, i.e., whether the processor 28 is currently operating in the remote terminal operating mode as illustrated and described hereinabove with respect to FIG. 7. If not, the process 350 loops back to the beginning of step 352. If, at step 352, the processor 28 determines that the pump 14 is operating in the remote terminal operating mode, the process 350 advances to step 354 where the processor 28 is operable to monitor the user keys 32. Thereafter at step 356, the processor 28 is operable to determine whether the user has pressed any of the user keys 32. If not, the process 350 loop back to step 354.

If, at step 356, the processor 28 determines that the user has pressed one of the user keys 32, the process 350 advances to step 358 where the processor 28 determines whether the key pad, i.e., the user keys 32, is currently locked. If so, the process 350 advances to step 360 where processor 28 is operable to control the display device 34 to display a key combination, i.e., a combination of the user keys 32, that unlocks the key pad. Thereafter at step 362, the processor 28 is operable to determine whether the user has entered the displayed key combination. If not, the process 350 loops back to step 360. If, at step 362 the processor 28 determines that the user has entered the displayed key combination, or if the processor 350 determines at step 358 that the user keys 32 are not locked, the process 350 advances to step 364 where the processor 28 exits the remote terminal operating mode, e.g., as described hereinabove.

The liquid infusion pump 14 provides for two different types of standard bolus, one of which is an immediate or so-called quick bolus that may be programmed locally or via the remote electronic device 12 when operating in the remote terminal mode described herein. For example, using the remote terminal operating mode described herein, by pressing and holding the up button 144 or the down button 146 in the remote terminal operating mode for several seconds, a beep sequence and vibration occur on the pump 14 and on the remote electronic device 12 after which a quick bolus screen appears on the display device 18. The user may press the up button 144 or the down button 146 to increment the displayed bolus amount until the desired bolus value is reached. In one embodiment, if the up button 144 was used to enter the quick bolus screen, the down button 146 must be used to increment the desired bolus value, and vice versa, although other button presses may be used to increment the desired bolus value in alternative embodiments. In any case, each press of the up button 144 or the down button 146 causes the pump 14 and the remote electronic device 12 to simultaneously beep and vibrate to indicate the incremental increase in the bolus amount. Five seconds after the last press of the up button 144 or the down button 146, the pump 14 and the remote electronic device 12 confirm the total quick bolus amount by illustratively activating one beep and vibration for each bolus increment that was programmed. The standard bolus symbol on the display device 18 then illustratively blinks for approximately five seconds, after which the pump 14 begins to deliver the programmed quick bolus. After the delay period, the pump 14 and the remote electronic device 12 beep and vibrate three times, and the pump 14 then begins to deliver the total quick bolus that was programmed. Illustratively, the display 18 simultaneously counts down the remaining bolus to be delivered until the full programmed quick bolus amount is delivered.

During programming, the quick bolus amount may be canceled by decrementing the quick bolus amount to 0.0 units using the opposite one of the up or down button 144, 146 that was used to increment the quick bolus amount. If the display remains at 0.0 units for approximately five seconds, no new bolus will be delivered and the pump display 18 returns to a RUN screen while the pump 14 and the remote electronic device 12 each beep and vibrate, e.g., three times. The quick bolus may also be canceled during confirmation of the total bolus amount (when one beep and vibration occurs for each bolus increment programmed) or during start delay (when the standard bolus symbol blinks for approximately five seconds), by pressing either of the up or down buttons 144, 146 respectively. When this occurs, the display device 18 returns to the RUN screen, and a bolus cancel warning then appears on the display 18. The user may press the OK or check button 150 twice to confirm and turn off the alert. The quick bolus may also be canceled during bolus delivery by pressing either the up button 144 or the down button 146 for approximately three seconds, after which a beep sequence will be activated on the pump 14 and on the remote electronic device 12, and the display 18 will display a bolus cancel warning. The OK or check button 150 may be pressed twice to confirm and turn off the alert.

Figure 12:
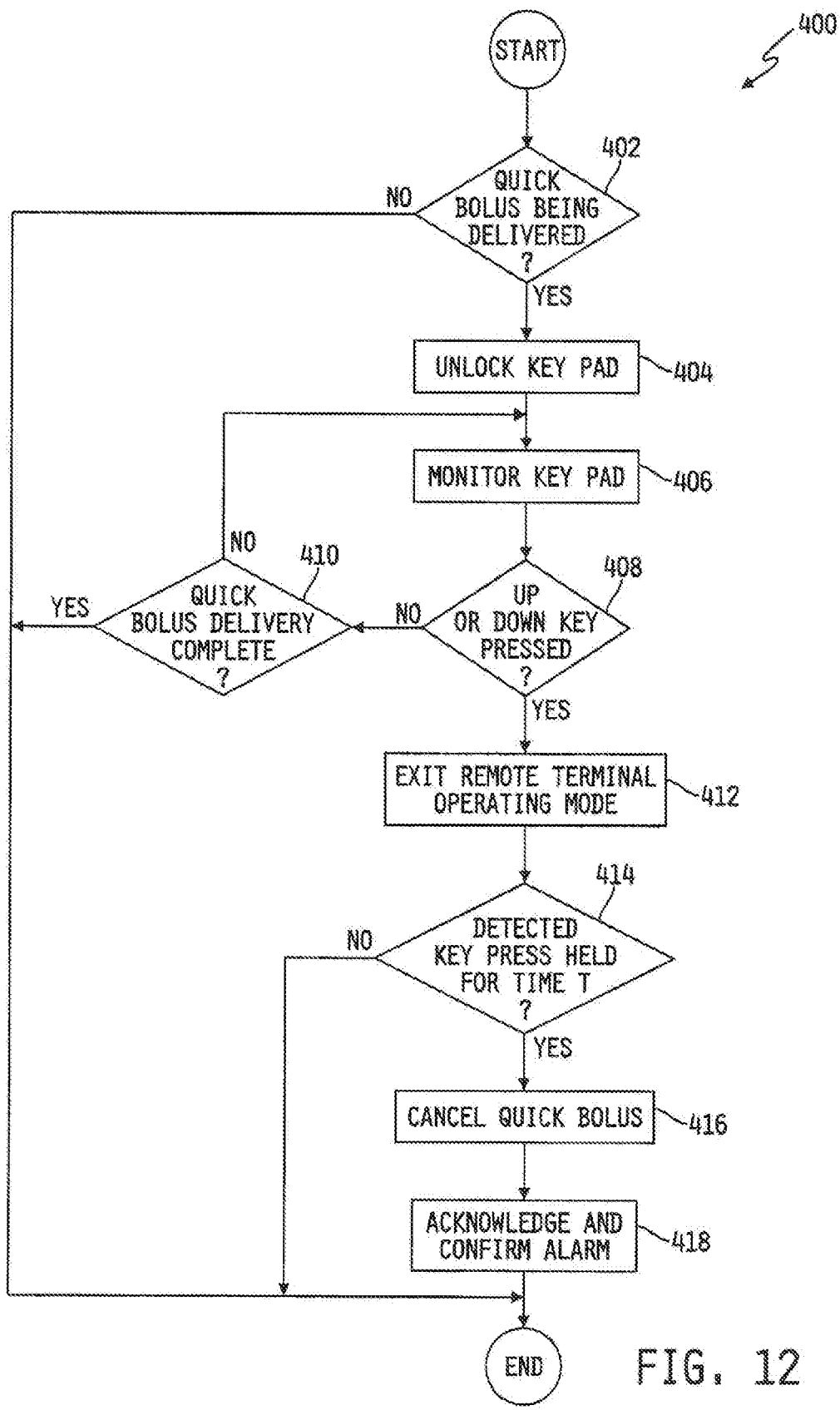
FIG. 12 shows a flowchart of one illustrative embodiment of a process that operates on the liquid infusion pump while delivering a quick bolus during the remote terminal operating mode.

When delivering a quick bolus as just described, the quick bolus may also be canceled via a user press and hold of one of the user keys 32 of the liquid infusion pump 14. Referring to FIG. 12, a flowchart is shown of one illustrative embodiment of such a process 400 that operates on the liquid infusion pump 14 during delivery of a quick bolus as just described. The process 400 is illustratively stored in the memory device 25 in the form of instructions that are executable by the processor 28 to carry out the process 400. In the illustrated embodiment, the process 400 presumes that the pump 14 is currently operating in the remote terminal operating mode as described herein, and the process 400 begins at step 402 where the processor 28 determines whether the pump 14 has been commanded to deliver a quick bolus. If so, the processor 28 is operable at step 404 to unlock the key pad, i.e., the user keys 32, on the pump 14. Thereafter at step 406, the processor 28 is operable to monitor the key pad, i.e., the user keys 32 of the pump 14. Thereafter at step 408, the processor 28 is illustratively operable to determine whether the up key 134 or the down key 136 has been pressed. In alternate embodiments, the processor 28 may be operable at step 408 to determine whether one or more other or additional keys have been pressed. In any case, if the processor 28 determines at step 408 that neither the up key 134 nor the down key 136 has been pressed, the process 400 advances to step 410 where the processor 28 determines whether delivery of the quick bolus is complete. If so, the process 400 ends. Otherwise, the process 400 loops back to step 406 to monitor the user keys 32.

If, at step 408, the processor 28 determines that the up key 134 or the down key 136 has been pressed, the process 400 advances to step 412 where the processor 28 is operable to exit the remote terminal operating mode, e.g., as described above. Thereafter at step 414, the processor 28 is operable to determine whether the key that was detected at step 408 as being pressed is held in the pressed position for a time T, e.g., 3 seconds. If not, the process 400 ends. If, at step 414, the processor 28 determines that the key that was detected at step 408 as being pressed is determined to have been further held for at least the time T, the process 400 advances to step 416 where the processor 28 is operable to cancel the quick bolus, i.e., to stop delivery by the pump 14 of the quick bolus. Thereafter at step 418, the warning or alarm that may accompany canceling of the quick bolus in some embodiments is acknowledged and confirmed as generally described above with the exception that the acknowledgement and confirmation process is, at step 418, carried out on the pump 14 using the user keys 32. Following step 418, the process 400 ends.

Figure 13:
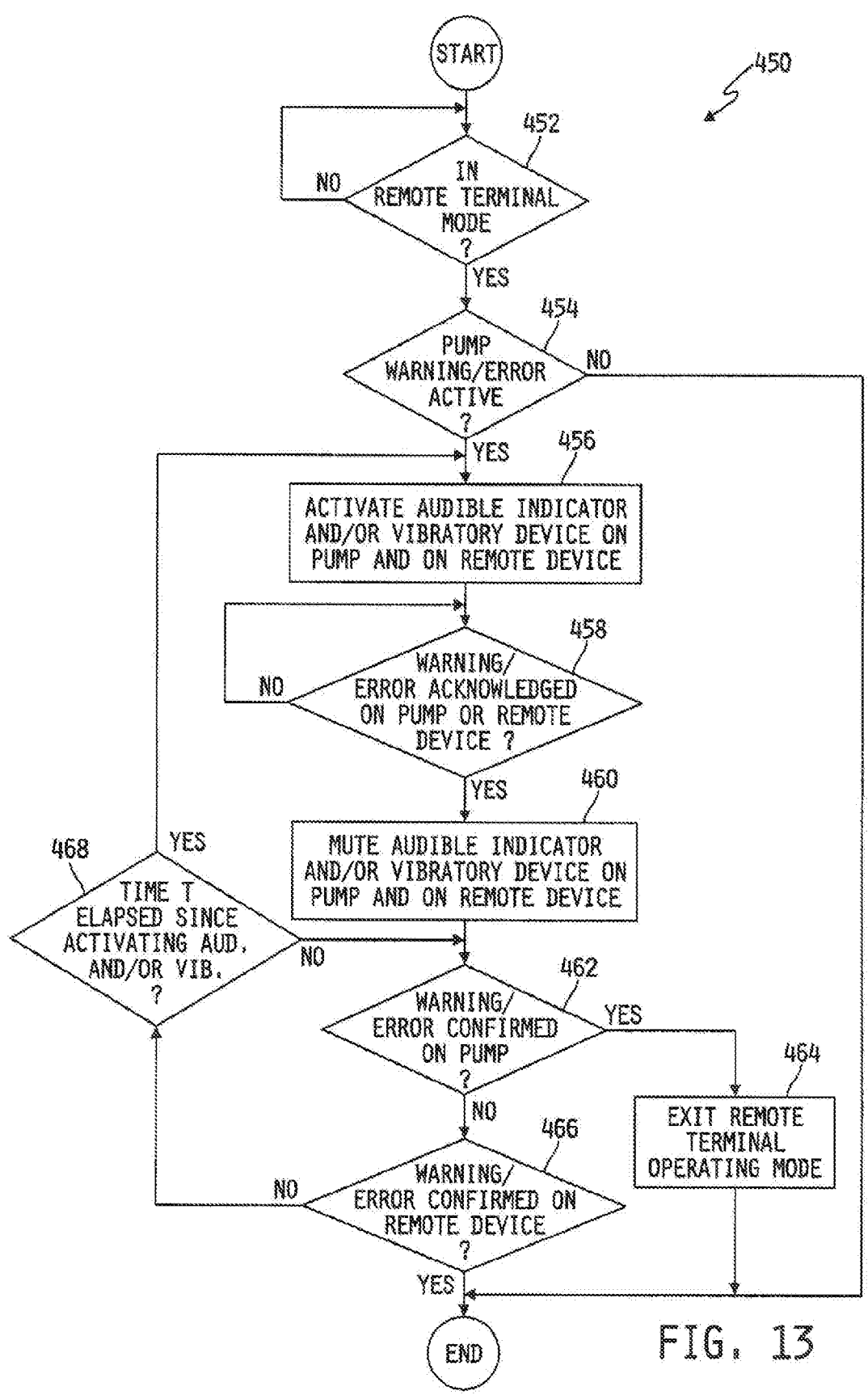
FIG. 13 shows a flowchart of one illustrative embodiment of a process that operates on the liquid, infusion pump and on the remote electronic device when a pump error or warning occurs during the remote terminal operating mode.

When operating in the remote terminal operating mode, warnings and errors associated with the operation of the liquid infusion pump 14 are acted upon by the pump 14, e.g., by activating the audible and/or vibratory devices 36, 38, and also by the remote electronic device 12 pursuant to instructions to do so by the processor 28, e.g., by likewise activating the audible and/or vibratory devices 72, 74 and/or by controlling the display 18 to display one or more suitable messages, as described above with respect to the process illustrated in FIG. 7. Acknowledgement and/or confirmation of any such errors or warnings may illustratively be addressed on the pump 14, e.g., via the user keys 32, and/or on the remote electronic device 12, e.g., via the user buttons 16, when operating in the remote terminal operating mode. Referring to FIG. 13, a flowchart is shown of one illustrative embodiment of such a process 450 that operates at least partially on the liquid infusion pump 14 and at least partially on the remote electronic device 12 during error and warning conditions associated with the pump 14 as just described. To the extent that the process 450 operates in the remote electronic device 12, this portion of the process 450 is illustratively stored in the memory device 66 in the form of instructions that are executable by the UI processor 50 to carry out the process 450. Likewise, to the extent that the process 450 operates in the liquid infusion pump 14, this portion of the process is illustratively stored in the memory device 25 in the form of instructions that are executable by the processor 28 to carry out the process 450.

The process 450 begins at step 452 where the processor 28 is operable to determine whether the pump 14 is currently in the remote terminal operating mode, i.e., whether the processor 28 is currently operating in the remote terminal operating mode as illustrated and described hereinabove with respect to FIG. 7. If not, the process 450 loops back to the beginning of step 452. If, at step 452, the processor 28 determines that the pump 14 is operating in the remote terminal operating mode, the process 450 advances to step 454 where the processor 28 is operable to determine whether a pump warning or error is active, i.e., whether a warning or error condition associated with the operation of the pump 14 is active. If so, the process 450 advances to step 456 where the processor 28 is operable to activate the audible and/or vibratory devices 36, 38, and to send a command, via the wireless communication circuit 30, to the UI processor 50 to likewise activate the audible and/or vibratory devices 72, 74. Thereafter at step 458, the processors 28 and 50 are both operable to determine whether the active warning or error has been acknowledged, e.g., via a suitable key or button press, on its respective device. In the illustrated embodiment, active warnings and errors may illustratively be acknowledged on the pump 14 or on the remote electronic device 12, e.g., via user press of the up key 134 or the down key 136 of the user keys 32 on the liquid infusion pump 14, or via user press of the up button 144 or the down button 146 of the user buttons 16 on the remote electronic device 12. If, at step 458, the processors 28 and 50 both determine that the active error or warning has not been acknowledged on the respective device 14, 12, the process 450 loops back to the beginning of step 458.

If, at step 458, the processor 28 or the processor 50 determines that the active error or warning of the pump 14 has been acknowledged on the pump 14 or the remote electronic device 12 respectively, the process 450 advances to step 460 where the processor 28 is operable to mute the audible and/or vibratory device 36, 38 and the processor 50 is likewise operable, at the command of the processor 28, to mute the audible and/or vibratory devices 72, 74. Thereafter at step 462, the processor 28 of the liquid infusion pump 14 is operable to determine whether the active pump error or warning has been confirmed on the pump 14 via pressing one or a simultaneous or other combination of the user keys 32, e.g., by a pressing the up key 134 or down key 136. If so, the process 450 advances to step 464 where the processor 28 is operable to exit the remote terminal operating mode, e.g., as described hereinabove. If, at step 462, the processor 28 determines that the active pump error or warning has not been confirmed on the pump 14, the process 450 advances to step 466 where the processor 50 of the remote electronic device 12 is operable to determine whether the active pump error or warning has been confirmed on the remote electronic device 12 via pressing one or a simultaneous or other combination of the user buttons 16, e.g., by a pressing the up button 144 or down button 146. If not, the process 450 advances to step 468 where the processors 28 and 50 are both operable to determine whether a time T, e.g., 60 seconds, has elapsed since activating the audible devices 36, 72 and/or the vibratory devices 38, 74. If not, the process 450 loops back to step 462. Otherwise, the process 450 loops back to step 456. From the "NO" branch of step 454, the "YES" branch of step 466 and from step 464, the process 450 ends.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, it will be understood that while various process embodiments have been described herein in which the medical device 14 is or includes a liquid infusion pump, all such processes may alternatively be used with other medical devices including, but not limited to, those specifically listed hereinabove.

What is claimed is:

1. An electronic device for remotely controlling a medical device having a first display device and a plurality of user keys, the electronic device comprising:
   a plurality of user buttons,
   a second display device at least as large as the first display device,
   a wireless communication circuit configured to wirelessly communicate with the medical device, and
   a processor including a memory having instructions stored therein that are executable by the processor to receive from the medical device via the wireless communication circuit screen data generated by the medical device for display on the first display device and to control the second display device according to the received screen data to display on the second display device all the screen data generated by the medical device, to emulate the plurality of user keys with selected ones of the plurality of user buttons, to control the second display device to display a map that relates emulated ones of the plurality of user keys to selected ones of the plurality of user buttons and to remotely control operation of the medical device via the wireless communication circuit based on user selection the plurality of buttons.

2. The electronic device of claim 1 wherein the instructions stored in the memory further include instructions that are executable by the processor to control the second display device to display navigation on the second display device by the selected ones of the plurality of user buttons and to display user selection of items on the second display.

3. The electronic device of claim 1 wherein the instructions stored in the memory further include instructions that are executable by the processor to send user selection of a single one of the plurality of user buttons to the medical device via the wireless communication circuit, to receive updated screen data from the medical device via the wireless communication circuit if implementation of the sent user selection causes the medical device to modify the screen data generated by the medical device, and to control the second display device according to the updated screen data.

4. The electronic device of claim 1 wherein the instructions stored in the memory further include instructions that are executable by the processor to receive updated screen data from the medical device via the wireless communication circuit if the operation of the medical device, apart from processing user selection of one of the plurality of user buttons, causes the medical device to modify the screen data generated by the medical device, and to control the second display device according to the updated screen data.

5. The electronic device of claim 1 wherein the medical device includes a liquid infusion pump.

6. The electronic device of claim 1 wherein the electronic device exits remote control operation of the medical device upon detection of a user press of at least one of the plurality of user keys if the plurality of user keys are unlocked.

* * * * *